US010434189B2

(12) United States Patent
Essani et al.

(10) Patent No.: US 10,434,189 B2
(45) Date of Patent: Oct. 8, 2019

(54) COMPOSITION FOR TREATING CANCEROUS CELLS AND A METHOD THEREFOR

(71) Applicant: The Board of Trustees of Western Michigan University, Kalamazoo, MI (US)

(72) Inventors: Karim Essani, Kalamazoo, MI (US); David Jeng, Kalamazoo, MI (US); Steven J. Conrad, Lansing, MI (US)

(73) Assignee: The Board of Trustees of Western Michigan University, Kalamazoo, MI (US)

( * ) Notice: Subject to any disclaimer, the term of this patent is extended or adjusted under 35 U.S.C. 154(b) by 28 days.

(21) Appl. No.: 15/407,912

(22) Filed: Jan. 17, 2017

(65) Prior Publication Data

US 2017/0165378 A1  Jun. 15, 2017

Related U.S. Application Data

(63) Continuation-in-part of application No. PCT/US2015/040881, filed on Jul. 17, 2015.

(60) Provisional application No. 62/025,734, filed on Jul. 17, 2014.

(51) Int. Cl.
| | | |
|---|---|---|
| A61K 48/00 | (2006.01) | |
| A61K 39/00 | (2006.01) | |
| A61K 35/768 | (2015.01) | |

(52) U.S. Cl.
CPC ........ *A61K 48/0066* (2013.01); *A61K 35/768* (2013.01); *A61K 39/00* (2013.01); *C12N 2710/24032* (2013.01); *Y02A 50/481* (2018.01); *Y02A 50/483* (2018.01)

(58) Field of Classification Search
None
See application file for complete search history.

(56) References Cited

U.S. PATENT DOCUMENTS

| | | | |
|---|---|---|---|
| 7,208,313 B2 | 4/2007 | McCart et al. | |
| 8,506,947 B2 | 8/2013 | McCart et al. | |
| 8,586,022 B2 | 11/2013 | Szalay et al. | |
| 8,679,509 B2 | 3/2014 | Evans et al. | |
| 8,691,502 B2 * | 4/2014 | Kupper | A61K 39/12 435/5 |
| 9,919,062 B2 * | 3/2018 | Kim | A61K 48/0066 |
| 2013/0108665 A1 | 5/2013 | Liang | |

FOREIGN PATENT DOCUMENTS

| | | |
|---|---|---|
| WO | 2004014314 A2 | 2/2004 |
| WO | 2010124393 A1 | 11/2010 |
| WO | 2016011336 A1 | 1/2016 |

OTHER PUBLICATIONS

Rahman et al. Virol 2009;386:462-8.*
Amann et al. J Gen Virol. 1995;76:1109-15.*
Nazarian et al. Virus Res 2007;129:11-25.*
Steven J. Conrad; Oncolytic Tanapoxvirus Expressing fliC Causes Regression of Human Colorectal Cancer Xenografts in Nude Mice; Dissertation; Jun. 2014; 2 pages; ScholarWorks at WMU; http://scholarworks.wmich.edu; last accessed Jan. 23, 2018.
Steven J. Conrad et al; Oncoselectivity in Oncolytic Viruses against Colorectal Cancer; Nov. 2014; 23 pages; Journal of Cancer Therapy; 5; 1153-1174. http://dx.doi.org/10.4236/jct.2014.513118.
David Jeng et al; The Tanapoxvirus 15L Protein is a Virus-Encoded Neuregulin that Promotes Viral Replication in Human Endothelial Cells; Mar. 2013; 9 pages; Journal of Virology; vol. 87, No. 6; p. 3108-3026. jvi.asm.org.
Norman Woller et al; Oncolytic Viruses as Anticancer Vaccines; Jul. 2014; 13 pages; Review Article; Frontiers in Oncology; vol. 4, Article 188. www.frontiersin.org.
European Patent Office; European Search Report in Application No. 15822175.4 / 3169342 PCT/US2015040881; dated Jan. 2, 2018; 7 pages; Munich, Germany.
Masmudur M. Rahman, et al., Variation in Ligand Binding Specificities of a Novel Class of Poxvirus-encoded Tumor Necrosis Factor-binding Protein, The Journal of Biological Chemistry, Aug. 11, 2006, pp. 22517-22526, vol. 281, No. 32.
Steven H. Nazarian et al., Tropism of Tanapox virus infection in primary human cells, Virology, 2007, pp. 32-40, vol. 368.
Masmudur M. Rahman et al., Interaction of human TMF and β2-microgolublin with Tanapox virus-encoded TNF inhibitor, TPV-2L, Virology, 2009, pp. 32-40, vol. 386.
A.C. Nichols et al., Vaccinia Virus Outperforms a Panel of Other Poxviruses as a Potent Oncolytic Agent for the Control of Head and Neck Squamous Cell Carcinoma Cell Lines, Intervirology, 2014, pp. 17-22, vol. 57, No. 1.
John Bell et al., Viruses for Tumor Therapy, Cell host & Microbe, 2014, pp. 260-265, vol. 15.
International Searching Authority, International Search Report and Written Opinion of the International Searching Authority for International Application PCT/US2015/040881 dated Oct. 29, 2015, 9 pages.
Steven J. Conrad et al., Oncolytic tanapoxvirus expressing FliC causes regression of human colorectal cancer xenografts in nude mice, Jouranl of Experimental & Clinical Cancer Research, 2015, 14 pages, vol. 34.

(Continued)

*Primary Examiner* — Robert M Kelly
(74) *Attorney, Agent, or Firm* — Price Heneveld LLP

(57) ABSTRACT

A composition for treating cancerous cells in a subject having an immune system includes a virus in the *Yatapoxvirus* genus having at least one mutation. In one embodiment, the mutation results in suppressed expression of a TNF binding protein by the virus. In another embodiment, the mutation results in suppressed expression of thymidine kinase ("TK") by the virus. In another embodiment, the mutation arms the virus with a transgene to express a bacterial flagellin. The mutations can be present singly or in combination. Additional aspects include a method of treating cancerous cells with a composition as described herein, and a method of delivering at least one gene to cancerous cells in a subject.

20 Claims, 25 Drawing Sheets

Specification includes a Sequence Listing.

(56) References Cited

OTHER PUBLICATIONS

Tiantian Zhang et al., Tanapoxvirus lacking a neuregulin-like gene regresses human melanoma tumors in nude mice, Virus Genes, 2016, 11 pages.

International Searching Authority; International Search Report and Written Opinion of the International Searching Authority in International Application No. PCT/US2018/014015; dated Jun. 28, 2018; 8 pages; Moscow, Russia.

* cited by examiner wtTPV

−◆− Mock  −■− wtTPV

Tumor volumes (mm³) vs Days post treatment

FIG. 5A

TPV/Δ66R/mIL2

- ♦ Mock
- ■ TPV/Δ66R/mIL-2

Tumor volumes (mm³) vs Days post treatment

FIG. 5D

TPV/Δ66R/FliC

- Mock
- TPV/Δ66R/fliC

Tumor volumes (mm³) vs Days post treatment

FIG. 5G

COMPOSITION FOR TREATING CANCEROUS CELLS AND A METHOD THEREFOR

CROSS-REFERENCE TO RELATED APPLICATIONS

This application is a Continuation-in-part of International Application No. PCT/US2015/040881, filed on Jul. 17, 2015, entitled "COMPOSITION FOR TREATING CANCEROUS CELLS AND A METHOD THEREFOR," the disclosure of which is hereby incorporated herein by reference in its entirety. PCT/US2015/040881 claims priority to U.S. Provisional Application No. 62/025,734, filed Jul. 17, 2014, entitled "COMPOSITION FOR TREATING CANCEROUS CELLS AND A METHOD THEREFOR," the disclosure of which is hereby incorporated herein by reference in its entirety.

STATEMENT REGARDING FEDERALLY SPONSORED RESEARCH OR DEVELOPMENT

This invention was made with government support under grant number CA156262 awarded by the National Institutes of Health. The government has certain rights in the invention.

FIELD OF THE INVENTION

The present disclosure relates to a composition for treating cancerous cells in subjects and a method therefor.

SUMMARY

One aspect of the present disclosure is a composition for treating cancerous cells in a subject having an immune system. The composition includes a virus in the *Yatapoxvirus* genus having at least one mutation. The at least one mutation results in suppressed expression of a TNF binding protein by the virus.

Another aspect of the present disclosure is a composition for treating cancerous cells in a subject having an immune system, including a virus in the *Yatapoxvirus* genus, where the virus has at least one mutation, the at least one mutation: resulting in suppressed expression of thymidine kinase ("TK"); resulting in suppressed expression of a TNF binding protein having a structure capable of binding an MHC-1 light chain; resulting in suppressed expression of a 15L-encoded protein mimicking neuregulin ("NRG"); and/or resulting in expression of interleukin-2 (IL-2), a T-cell growth factor.

In another aspect of the present disclosure, the composition for treating cancerous cells in a subject having an immune system includes a poxvirus which encodes a transgene expressing a bacterial flagellin.

In yet another aspect of the present disclosure, a method of treating a subject with cancerous cells includes administering a composition to the subject, wherein the composition includes: a virus in the *Yatapoxvirus* genus having at least one mutation which results in suppressed expression of a TNF binding protein having a structure capable of binding an MHC-1 light chain by the virus; a virus in the *Yatapoxvirus* genus having at least one mutation which results in suppressed expression of thymidine kinase ("TK"); a virus in the *Yatapoxvirus* genus having at least one mutation which results in suppressed expression of a 15L-encoded protein mimicking neuregulin ("NRG"); and/or a virus in the *Yatapoxvirus* genus having at least one mutation which results in expression of interleukin-2 (IL-2), a T-cell growth factor.

According to yet another aspect of the present disclosure, at least one gene is delivered to cancerous cells in a subject by modifying a virus of the *Yatapoxvirus* genus by mutating the virus to: suppress expression of a TNF binding protein having a structure capable of binding an MHC-1 light chain; suppress expression of thymidine kinase ("TK"), suppress expression of a 15L-encoded protein mimicking neuregulin ("NRG"); and/or express interleukin-2 (IL-2), a T-cell growth factor. The virus is also modified by encoding at least one gene in the virus, wherein the at least one gene encoded in the virus results in increased apoptosis of the cancerous cells or activates an immune response in the subject. The modified virus is administered to the subject.

The pharmaceutical compositions for treating cancerous tumors and methods described herein allow for potentially effective treatment of the cancerous cells with limited risk of serious infection or side effects which may be experienced with traditional treatment methods, and may in some cases be used in combination with traditional treatment methods. The modified poxviruses described herein have exhibited results which indicate increased oncoselectivity and increased oncolethality as compared to unmodified poxviruses, and are expected to maintain preferable OV characteristics such as causing only a mild and self-limiting febrile illness in infected subjects.

These and other features, advantages, and objects of the present disclosure will be further understood and appreciated by those skilled in the art upon studying the following specification, claims, and appended drawings.

BRIEF DESCRIPTION OF THE DRAWINGS

FIG. 5A is a graph illustrating average tumor volume in athymic nude mice xenografted with MDA-MB-231 cells and treated with a wild-type TPV (wtTPV) as compared to a vehicle-only control solution;

FIG. 5D is a graph illustrating average tumor volume in athymic nude mice xenografted with MDA-MB-231 cells and treated with one embodiment of recombinant TPV (TPV-p2KO/Δ66R/mIL2) as compared to the vehicle-only solution;

FIG. 5G is a graph illustrating average tumor volume in athymic nude mice xenografted with MDA-MB-231 cells and treated with one embodiment of recombinant TPV (TPV-p2KO/Δ66R/FliC) as compared to the vehicle-only solution;

DETAILED DESCRIPTION

Figure 1:
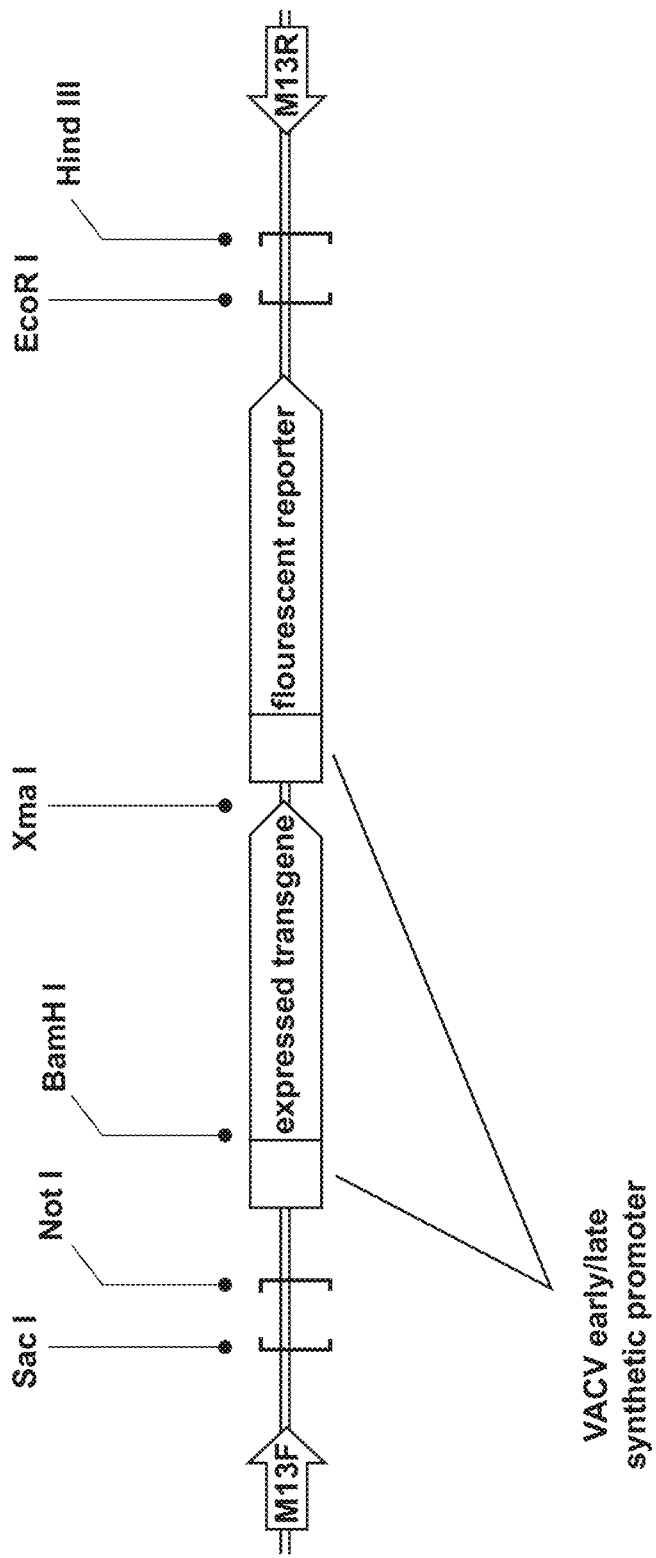
FIG. 1 is a schematic illustrating one embodiment of a recombinant tanapoxvirus (TPV) as altered by a p2KO method to insert an expressed transgene and a fluorescent reporter.

For purposes of description herein the terms "upper," "lower," "right," "left," "rear," "front," "vertical," "horizontal," and derivatives thereof shall relate to the composition as oriented in FIG. 1. However, it is to be understood that the composition may assume various alternative orientations and the methods may include various step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Although some preference for infection of cancerous and/or transformed cells has been shown in oncolytic variants of some viruses such as VACV, wild-type poxviruses such as those in the genus *Yatapoxvirus*, including without limitation tanapoxvirus ("TPV"), are not generally considered to have a high degree of native oncospecificity. In viruses without significant native oncospecificity, genetic engineering has been employed to increase cancer cell selectivity.

Although they do not necessarily have a high degree of native oncospecificity, poxviruses, and more specifically poxviruses in the *Yatapoxvirus* genus, have several inherent qualities that make them well-suited for modification for use as OVs. Poxviruses have viral genomes which are able to accommodate a large amount of added genetic material, and come with a built-in array of offensive and defensive capabilities. Poxvirus genomes encode a variety of immunomodulatory proteins devoted to hiding infection-associated cell-surface epitopes from host immunesurveillance, the inhibition and evasion of some host immune and inflammatory responses, and the disruption of signals from the extracellular environment by means of virally-encoded peptides which mimic host cytokines and cytokine receptors.

Poxviruses also produce two distinct types of progeny virions, the mature virion (MV) form and the enveloped virion (EV) form. The MV form of the virus is enclosed in a single lipid bilayer and is released from the host cell only by cytolysis. The EV form is actively exported from the host cell after it has acquired a second, outer envelope, possibly from the host cell trans Golgi network, and is referred to as a wrapped virion (WV) until it is exported from the infected cell, after which time it is referred to as the EV form. The poxvirus EV form is a specialized form of the virus which is responsible for spreading the poxvirus to distant sites within the host by trafficking through the bloodstream and the lymphatic network. The EV form is well-suited for this task, as it has only 6 transmembrane proteins exposed to the extracellular environment vs. approximately 20 for the MV form. Fewer exposed epitopes mean that the EV form is more able to escape neutralizing immunity than the MV form.

Additionally, TPV, a member of the genus *Yatapoxvirus* and a wild poxvirus, has additional features which are beneficial in developing an OV, making it a preferred member of the *Yatapoxvirus* genus for developing an OV. Humans infected with TPV experience only a mild and self-limiting febrile illness, possibly because TPV infection is normally confined to peripheral areas of the body. Apart from areas in equatorial Africa (where it is endemic) humans are immunologically naïve to TPV. Additionally, the TPV has never been observed to transmit from person to person, a highly desirable safety feature in an OV.

Genetically engineered specimens of poxviruses, including specimens of the *Yatapoxvirus* genus, are disclosed herein for use as OV, to be incorporated in compositions to treat cancerous cells, and to be used in methods of treating cancerous cells. Several preferred embodiments, including several preferred embodiments incorporating a recombinant TPV, are also described herein.

In summary, as further described below, one aspect of the present disclosure is a composition for treating cancerous cells in a subject having an immune system. In one aspect, the composition includes a virus in the *Yatapoxvirus* genus having at least one mutation. The at least one mutation results in suppressed expression of a TNF binding protein by the virus. Another aspect of the present disclosure is a composition for treating cancerous cells in a subject having an immune system, including a virus in the *Yatapoxvirus* genus, where the virus has at least one mutation resulting in suppressed expression of thymidine kinase ("TK"). Another aspect of the present disclosure is a composition for treating cancerous cells in a subject having an immune system, including a virus in the *Yatapoxvirus* genus, where the virus has at least one mutation resulting in suppressed expression of a 15L-encoded protein mimicking neuregulin ("NRG"). Yet another aspect of the present disclosure is a composition for treating cancerous cells in a subject having an immune system, including a virus in the *Yatapoxvirus* genus, where the virus has at least one mutation resulting in expression of interleukin-2 (IL-2), a T-cell growth factor. In another aspect, the composition includes a poxvirus which encodes a transgene expressing a bacterial flagellin. As used herein, the term "subject" includes human and animal subjects, and preferably mammalian subjects.

Also as described in greater detail below, a method of treating a subject having cancerous cells includes administering a composition to the subject, wherein the composition is as described herein. For example, in one embodiment the composition includes a virus in the *Yatapoxvirus* genus having at least one mutation which results in suppressed expression of a TNF binding protein by the virus. In another embodiment, the composition includes a virus in the *Yatapoxvirus* genus, where the virus has at least one mutation resulting in suppressed expression of TK. In another embodiment, the composition includes a virus in the *Yatapoxvirus* genus, where the virus has at least one mutation resulting in suppressed expression of a 15L-encoded protein mimicking neuregulin ("NRG"). In another embodiment, the composition includes a virus in the *Yatapoxvirus* genus, where the virus has at least one mutation resulting in expression of interleukin-2 (IL-2), a T-cell growth factor. In yet another embodiment, the composition includes a poxvirus which is encodes a transgene expressing a bacterial flagellin. Any or all of these mutations can be present in the composition, singly or in any combination. Additionally, the composition can be delivered in a targeted manner to a group of cancerous cells, or can be delivered to the subject systemically.

According to yet another aspect of the present disclosure, as described in greater detail below, at least one gene is delivered to cancerous cells in a subject by modifying a virus of the *Yatapoxvirus* genus by mutating the virus to: suppress expression of a TNF binding protein having a structure capable of binding an MHC-1 light chain; suppress expression of thymidine kinase ("TK"), suppress expression of a 15L-encoded protein mimicking neuregulin ("NRG"); and/or express interleukin-2 (IL-2), a T-cell growth factor. The virus is also modified by encoding at least one gene in the virus, wherein the at least one gene encoded in the virus results in increased apoptosis of the cancerous cells or activates an immune response in the subject. The modified virus is administered to the subject.

In certain embodiments, the poxvirus is genetically modified to suppress expression of a host range factor with TNF-binding activity, also referred to herein as a TNF binding protein. The TNF binding protein which is suppressed is similar in structure to an MHC-1 heavy chain protein, and the encoded TNF binding protein can interact with an MHC-1 light chain. In TPV, the TNF binding protein is encoded in the 2L gene. Recombinant TPV in which the 2L gene has been ablated or otherwise mutated to suppress expression of the TNF binding protein is sometimes referred to herein as "2L-deleted" or "Δ2L." In a normal poxvirus infection, secreted TNF binding protein acts to blunt the host inflammatory and antiviral immune response by binding to and effectively reducing the amount of TNF present to interact with the infected cells. While this is a desirable outcome for the poxvirus, when poxvirus is used as an OV it may be advantageous to increase, rather than decrease, the amount of inflammation experienced by the treated tumor. In a human subject whose tumor is treated with an OV based upon the recombinant TPV as the poxvirus, ablation of the 2L gene in the recombinant TPV can result in an effective increase in TNF concentration at the tumor site, (compared to tumors infected with 2L-bearing TPV). Increased levels of TNF can ultimately act to increase tumor clearance. Because the 2L gene has previously been shown to bind to human TNF but not mouse TNF, the ablation of the 2L gene in some of the recombinant TPVs described herein was not expected to be a significant factor in tumor clearance during the mouse experiments, but is expected to be a more significant factor in tumor clearance in primates and humans. Ablation of the 2L gene was undertaken in the specific examples of the recombinant TPV used in xenografted athymic nude mice where the xenograft is made up of human cancer cells, as described herein, because mouse testing is an important step towards further testing of poxvirus-based OVs in more relevant primate models of cancer virotherapy.

In certain embodiments, the oncoselectivity of the poxvirus is increased by modifying the poxvirus to suppress expression of thymidine kinase (TK). In TPV, the TK encoding gene is known as 66R. Recombinant TPV in which the 66R gene has been ablated or otherwise mutated to suppress expression of TK is sometimes referred to herein as "66R-deleted" or "Δ66R." The TK activity in neoplastic cells is constitutively high, due to the action of the cellular TK1 in cancerous cells. This is in contrast to normal cells, where TK activity levels peak during the S phase of the cell cycle and are nearly undetectable at other times. Cellular TK1 catalyses a step in nucleotide synthesis, the conversion of thymidine to thymidine monophosphate. For this reason, cancerous cells express TK1 throughout the cell cycle, and as a result tend to have large cytoplasmic pools of thymidine monophosphate available at all stages of the cell cycle. By suppressing the TK encoding gene, particularly in poxviruses in the *Yatapoxvirus* genus, the poxvirus has greater cancer cell selectivity than if the TK encoding gene was left intact. Ablation of the 66R gene was undertaken in some of the specific examples of the recombinant TPV used in xenografted athymic nude mice described herein even though mice are not normally animal hosts for TPV. Ablation of the 66R gene in this environment demonstrates that the ablation of the 66R gene did not result in non-replicative TPV in permissive cells (such as the human cancerous tumor cells).

In some embodiments, the poxvirus is genetically modified to suppress expression of a 15L-encoded protein that mimics neuregulin ("NRG"). Recombinant TPV in which the 15L gene has been ablated or otherwise mutated to suppress expression of the protein mimicking neuregulin is sometimes referred to herein as "15L-deleted" or "Δ15L." The 15L-encoded protein biologically mimics neuregulin and may act as an epidermal growth factor (EGF). The 15L-encoded protein and/or NRG may act as a ligand for ErbB3 and ErbB4 which are associated with therapeutic resistance in many cancers, such as melanoma, breast cancer, and prostate cancer. The binding of ligands to the ErbB receptors leads to formation of homo- or heterodimers and the activation of the intrinsic kinase domain. These activities, in turn, initiate a signal transduction cascade that ultimately leads to DNA synthesis and cell proliferation. By suppressing the expression of the 15L-encoded protein, which mimics the NRG, particularly in poxviruses in the *Yatapoxvirus* genus, the poxvirus has the ability to regress the growth of tumors compared to the 15L encoding gene left intact. Ablation of the 15L gene was undertaken in some specific examples of the recombinant TPV and used in xenografted athymic nude mice described herein even though mice are not normally hosts for TPV. Ablation of the 15L gene in a recombinant TPV, either alone or in combination with other genetic modifications, demonstrates that the ablation of the 15L gene can regress human melanoma, breast, and colorectal tumors in nude mice.

In still other embodiments, the poxvirus is genetically modified to express interleukin-2 (IL-2), a T-cell growth factor. Interleukin-2 (IL-2), a T-cell growth factor, plays a critical role in activating T cells, natural killer (NK) cells, and macrophages in both the innate and adaptive immune system. Recombinant TPV in which the (mIL-2) gene has been introduced may increase the poxvirus anti-tumor activity, resulting in more significant melanoma regression than wild-type TPV. IL-2 is a pleiotropic cytokine that plays a key role in both the innate and adaptive immune systems. IL-2 is secreted by T cells and induces differentiation and development of thymic lymphocytes to become effector T cells. IL-2 has been shown to promote the survival of memory $CD8^+$ T cells and enhance MHC-II expression on tumor cells. In adoptive T cell transfer therapy which has demonstrated consistent efficacy in treating melanoma, IL-2 has been used for expanding T cells in vitro before reinfusing the T cells back into cancer patients. In addition, IL-2 possesses substantial efficacy in activating the innate immune system. It has been demonstrated that IL-2 activates natural killer (NK) cells to acquire enhanced cytotoxic functions (known as lymphokine-activated killing [LAK]). NK cells activated by IL-2 have been shown to target tumor cells in a broader spectrum with an increased affinity of perforin for the tumor cells, which resulted in more significant cell lysis. Additionally, it has been demonstrated that macrophages, after being activated by IL-2, become larger, more granular and conglomerated on the cancer cells with enhanced cytotoxicity. IL-2 has also been shown to activate macrophages to induce tumor necrosis factor (TNF) and other cytotoxic molecules such as free radicals. By adding and expressing the mIL-2 gene, particularly in poxviruses in the *Yatapoxvirus* genus, the poxvirus has the ability to increase the poxvirus anti-tumor activity, resulting in more significant melanoma regression. Introduction of the mIL-2 gene was undertaken in some specific examples of the recombinant TPV used in xenografted athymic nude mice described herein even though mice are not normally hosts for TPV. Addition of the mIL-2 gene in a recombinant TPV, either alone or in combination with other genetic modifications, demonstrates that the introduction of the mIL-2 gene can increase anti-tumor activity in human melanoma, breast, and colorectal tumors in nude mice.

In additional embodiments, the poxvirus may be genetically modified to express other immune stimulatory proteins such as a monocyte chemotactic protein 1 (mCCL2) and/or a granulocyte monocyte colony stimulating factor (mG-MCSF). The monocyte chemotactic protein 1 may act as a potent inflammatory chemoattractant for memory T cells (CD29+ and CD45RO+), B cells, dendritic cells, monocytes, and/or macrophages. The granulocyte monocyte colony stimulating factor may act towards the induction of anti-tumor cytotoxic lymphocyte (CTL) responses. By adding and expressing the mCCL2 and/or mGMCSF genes, particularly in poxviruses in the *Yatapoxvirus* genus, the poxvirus has the ability to increase the poxvirus anti-tumor activity, resulting in more significant tumor regression. Introduction of the mCCL2 and/or mGMCSF gene was undertaken in some specific examples of the recombinant TPV used in xenografted athymic nude mice described herein even though mice are not normally hosts for TPV. Addition of the mCCL2 and/or mGMCSF gene in a recombinant TPV, either alone or in combination with the other genetic modifications mentioned herein, demonstrates that the introduction of the mCCL2 and/or mGMCSF gene may increase anti-tumor activity in human melanoma, breast, and colorectal tumors in nude mice.

Additionally, the oncolethality of the poxviruses can be increased by encoding the poxvirus with transgenes to increase apoptosis of the cancer cells or to activate the immune system of the subject. Examples of transgenes which can be used to encode the poxvirus include without limitation genes to express cytokines, chemokines, antigen-presenting polypeptides, or bacterial antigens. As used herein, cytokine refers to a protein or a polypeptide having immune cell or system modulating effects, such as stimulating immune cells, promoting growth of immune cells, or directing immune cells to a particular site. In certain preferred embodiments, the poxvirus used is recombinant TPV, armed with a granulocyte-monocyte colony stimulating factor (GM-CSF), macrophage chemotactic protein 1 (CCL2, also referred to as MCP-1 and MCF-1), or bacterial flagellin (FliC, the product of the fliC gene in *Salmonella enterica*). When experimenting with recombinant TPV for use with mice, the mouse (m) version of these transgenes was used where relevant in the recombinant TPV, i.e., mGM-CSF, mCCL2, mMCP1, mMCF-1. It is preferred to use the appropriate or effective versions of these transgenes for the subject upon which testing or treatment will be carried out.

Polymerized flagellin is the main component of the bacterial flagellum for use according to the present disclosure. The flagellin used for the specific experiments described herein was the product of the *Salmonella enterica serovar typhimurium* gene, fliC. FliC and other bacterial flagellins are cognate ligands of the toll-like receptor 5 (TLR5), and are strong activators of the innate immune response in mammalian cells via MyD88-dependent intracellular signaling and, ultimately, the activation of transcription factor NFκB. The flagellins are potent and pleiotropic virulence factors which have other important roles in bacterial pathogenesis.

In addition to the modification of the genome in the poxvirus embodiments described above, a fluorescent reporter transgene is optionally inserted into the genome of the poxvirus. Visualization of viral infection in cultured cells is greatly facilitated by the inclusion of the fluorescent reporter transgene, thereby facilitating research using the poxvirus variants described herein. Preferred fluorescent reporter transgenes include the reporters mCherry (excitation/emission 587 nm/610 nm) and enhanced green fluorescent protein (GFP, excitation/emission 475 nm/509 nm).

Preferred embodiments of the poxvirus include viruses, preferably of the *Yatapoxvirus* genus, having any or all of the mutations or insertions described above, and the mutations and insertions are preferably carried out using a p2KO vector method. In one preferred embodiment, recombinant TPV, a member of the *Yatapoxvirus* genus, is altered by the p2KO method as used herein, a schematic of which is shown in FIG. 1. As illustrated, two vaccinia virus (VACV)-derived early/late synthetic promotors are used to drive the expression of the desired expressed transgene to encode the virus (e.g., mGM-CSF, mCCL2, mMCP1, mMCF-1, fliC) and the optional fluorescent reporter transgene. The embodiment of the p2KO vector method depicted in FIG. 1 includes transferring a p2KO expression cassette (including left and right flanks, at least one intervening open reading frame (ORF) including the expressed transgene or the fluorescent reporter transgene, and at least one promoter) to the viral genome of the TPV through a homologous recombination double-crossover event during a transfection/infection procedure as described in greater detail below. In this way, the p2KO expression cassette is guided to a specific point in the viral genome of the TPV by the use of viral genomic flanking sequences, resulting in a targeted ablation of the desired gene(s) with the simultaneous expression of the desired expressed transgene and optional fluorescent reporter transgene in the recombinant TPV.

In the embodiment of the TPV p2KO expression cassette as illustrated in FIG. 1, a plurality of poxvirus early/late synthetic promotors allowed for the expression of multiple transgenes. The p2KO expression cassette guided insertion to a specific point in the viral genome by use of viral genomic flanking sequences derived from a target gene, resulting in the targeted ablation of the desired gene(s) with the simultaneous expression of the fluorescent reporter transgene and the expressed transgene to arm the virus. In the embodiment shown in FIG. 1, both a fluorescent reporter transgene and expressed transgene are shown. In alternate embodiments, either of the fluorescent reporter transgene or the expressed transgene could be present in the p2KO expression cassette for insertion into the viral genome. The left and right flanks are bounded by pairs of unique restriction sites. The flanking regions are ligated into a p2KO vector between a Sac I restriction site and a Not I restriction site on a 5'-(left) flank, and between a EcoR I restriction site and a Hind III restriction site on the 3'-(right) flank. The gene(s) to be expressed (the fluorescent reporter and/or the expressed transgene) are bounded by a unique 5'-BamH I restriction site and a 3'-Xma I restriction site. These allow for the simple and directional ligation of PCR amplicons bounded by the appropriate restriction sites.

Relevant primers used in the p2KO method for the examples described herein are shown in Table 1, below. In each case, an inserted restriction endonuclease site is indicated by underlining. Where applicable, in a forward primer the start codon is indicated in bold with grey shading and in a reverse primer a stop codon is indicated in bold with grey shading. Left and right flank primers used in the examples described herein did not include start or stop codons.

TABLE 1

Primers used to prepare the p2KO ablation/insertion vector

| Primer name | sequence |
|---|---|
| left flank | |
| 66R L SacI (f) | 5'-AATGGATCACATAAAG<u>GAGCTCT</u>TAACG-3' |
| 66R L NotI (r) | 5'-CAGAAAACAT<u>GCGGCCGC</u>ATATAATCT-3' |
| 15L L XhoI (f) | 5'-TAGGTA<u>CTCGAG</u>AAAAACACCAATA-3' |
| 15L L ClaI (r) | 5'-GTTTAA<u>ATCGAT</u>GGACCTG-3' |
| right flank | |
| 66R R EcoRI | 5'-GGAGATGAACAAGAAATA<u>GAATTC</u>ATAGG-3' |
| 66R R HindIII | 5'-CTGTTCTTTATCAC<u>AAGCTT</u>CTATCGGGTG-3' |
| 15L R NotI (f) | 5'-CATATTTT<u>GCGGCCGC</u>GGTAAACAATT-3' |
| 15L R (r) | 5'-GTTAAAAATGGAAAA<u>GAGCTC</u>TAATTTTAACAACAG-3' |

TABLE 1-continued Primers used to prepare the p2KO ablation/insertion vector

| Primer name | sequence |
|---|---|
| mGM-CSF | |
| hmGMCSF BamHI (f) | 5'-TAGGCCTGG<u>GGATCC</u>GATCCACCGGTCGCCACCATGTGGCTGCAGA-3' |
| mGMCSF XmaI (r) | 5'-CTCATCAATGTATCTTATCAT<u>CCCGGG</u>CTAGCT-3' |
| mCCL2/MCP-1 | |
| mMCP-1 BamHI (f) | 5'-TAGGCCTGG<u>GGATCC</u>GATCCACCGGTCGCCACCATGCAGGTCCCTC-3' |
| mMCP-1 XmaI (r) | 5'-CGGCGATC<u>CCCGGG</u>AGATACTAGTTCAC-3' |
| fliC (*S. typhimurium*) | |
| FliC BamHI (f) | 5'-ACCCGG<u>GGATCC</u>TCTAGAAATAATTTTG-3' |
| FliC XmaI (r) | 5'-GGAGCTCGAA<u>CCCGGG</u>TCCTTAAC-3' |
| M13 (f) | 5'- |
| M13 (r) | 3'- |

The ORFs used in various embodiments of the p2KO method for an expressed transgene insertion site include the mCCL2 transgene, the mGM-CSF transgene, and the fliC transgene. The mCCL2 transgene used in the examples cited below was produced using a mCCL2 cDNA clone ORF purchased as an ORF-bearing plasmid (available from Sino Biological, Incorporated). The mGM-CSF transgene used in the examples cited below was produced using a cDNA clone ORF of mGM-CSF provided by Dr. Grant McFadden. The mCCL2, mGM-CSF and fliC ORFs were amplified from their vectors by PCR and given a BamHI restriction sequence and an XmaI restriction sequences on the 5'- and 3'-termini of the product amplicons, respectively. The mCCL2, mGM-CSF, and fliC ORFs were ligated into the p2KO ablation/insertion vector.

The following abbreviations, as shown in Table 2 below, are used herein to describe various embodiments of the recombinant TPV which were produced using the p2KO method. Although the p2KO ablation/insertion method is described herein, it is understood that any method known for ablating genes from the genome or inserting transgenes into the genome can be used to form the recombinant TPV described herein.

TABLE 2

Recombinant TPV abbreviations

| TPV recombinant | gene ablated | gene added | reporter(s) |
|---|---|---|---|
| TPV/egfp | — | — | EGFP |
| TPV-p2KO/Δ66R | 66R | — | mCherry |
| TPV-p2KO/Δ66R/mGM-CSF | 66R | mGM-CSF | mCherry |
| TPV-p2KO/Δ66R/mMCP-1 | 66R | mMCP-1 | mCherry |
| TPV-p2KO/Δ66R/fliC | 66R | fliC | mCherry |
| TPV-p2KO/Δ2L | 2L | — | mCherry |
| TPV-p2KO/Δ2L/Δ66R/fliC | 66R, 2L | fliC | EGFP, mCherry |
| TPV-p2KO/Δ15L | 15L | — | EGFP |
| TPV-p2KO/Δ66R/Δ15L | 66R, 15L | — | EGFP, mCherry |
| TPV-p2KO/Δ66R/mIL-2 | 66R | mIL-2 | mCherry |
| TPV-p2KO/Δ66R/Δ2L | 66R, 2L | — | mCherry |
| TPV-p2KO/Δ66R/mCCL2 | 66R | mCCL2 | mCherry |
| TPV-p2KO/Δ66R/mGMCSF | 66R | mGMCSF | mCherry |

To choose an appropriate cell line for testing the recombinant TPV in mouse hosts, the minimally-altered recombinant TPV/egfp was tested against a panel of human colorectal cancer cell lines to select the cell line which allowed the best viral replication, thereby maximizing the effect of direct viral tumor cell lysis. The hCRC cell lines tested for TPV/egfp replication included HCT 116, COLO205, SW1463 and WiDr. Viral lysis of tumor cells is of importance to tumor clearance in some cases, but viral cytolysis is only one of many factors impinging upon tumor survival and clearance, and immune cell recruitment can also play a role. Although HCT 116 produced fewer progeny virions than the control cell line OMK, HCT 116 was the most productive of the hCRC cell lines tested. Additionally, many OVs have been characterized in tumors induced with HCT 116. For these reasons HCT 116 was used for experiments to further characterize the oncolytic potential of the recombinant TPV in vivo.

To evaluate various embodiments of recombinant TPV, tumors were induced in athymic nude mice with the HCT 116 cell line by subcutaneous injection of $5 \times 10^6$ HCT 116 cells onto a dorsal surface of the athymic nude mice. The mice were randomly segregated into control or experimental groups when tumor size reached 75 mm$^3$, with 5 mice in each group. A single injection containing 100 L of vehicle only (group a) or recombinant TPV (groups b-h) was administered at day 0 (after reaching the tumor volume of 75 mm$^3$) and tumor volume was measured at three-day intervals thereafter. The average tumor volume was calculated using the formula:

$$\text{Average tumor volume} = (\text{length}) \times (\text{width}) \times (\text{height}) \times \pi/6 \quad (1)$$

The HCT 116-induced tumor xenografts did not increase in volume to the expected level during treatment with the recombinant TPV. However, multiple secondary tumors developed in mice undergoing treatment with the recombinant TPV. Additionally, in some in vitro studies, including an HCT 116 orthotopic xenotransplant model, HCT 116 cells have been reported to be highly motile and invasive.

Figure 2A:
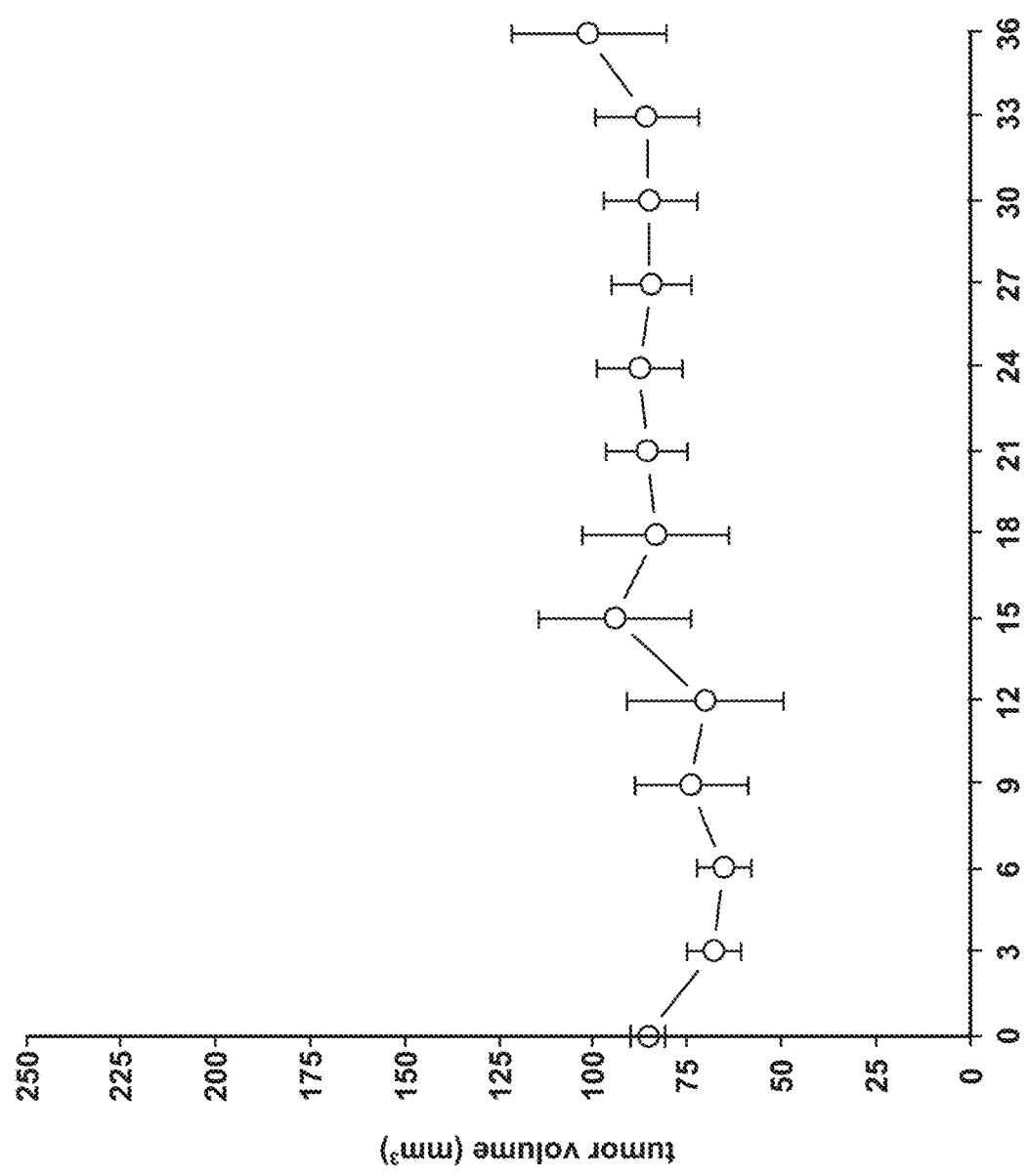
FIG. 2A is a graph illustrating average tumor volume in athymic nude mice xenografted with HCT 116 cells and treated with a vehicle-only control solution.

FIG. 2A illustrates the observed average tumor development over a span of 36 days (beginning at the time when the tumor mass exceeded 75 mm$^3$) in athymic nude mice xenografted with 5×10$^6$ HCT 116 cells and subsequently treated with a vehicle only control solution. The average tumor volume, shown in an open circle, increased until approximately 15 days, at which point its volume stabilized at approximately 100 mm$^3$ for the remainder of the time span. The standard error of the mean is shown with bars (+/−1 SEM). The stabilization of the volume of the tumor is in contrast to some previous studies which have shown that untreated HCT 116 tumors in nude mice gradually increase in volume over the same interval, when using the same or similar numbers of HCT 116 cells in the initial xenograft. For example, it has been reported that HCT 116-induced tumors have a doubling time of approximately 8 days. Also, a recent study which examined the VACV as an OV therapeutic against HCT 116 xenografts in nude mice showed HCT 116 tumor growth up to 4000 mm$^3$ in a time interval similar to the time span illustrated in FIG. 2A.

Figure 2B:
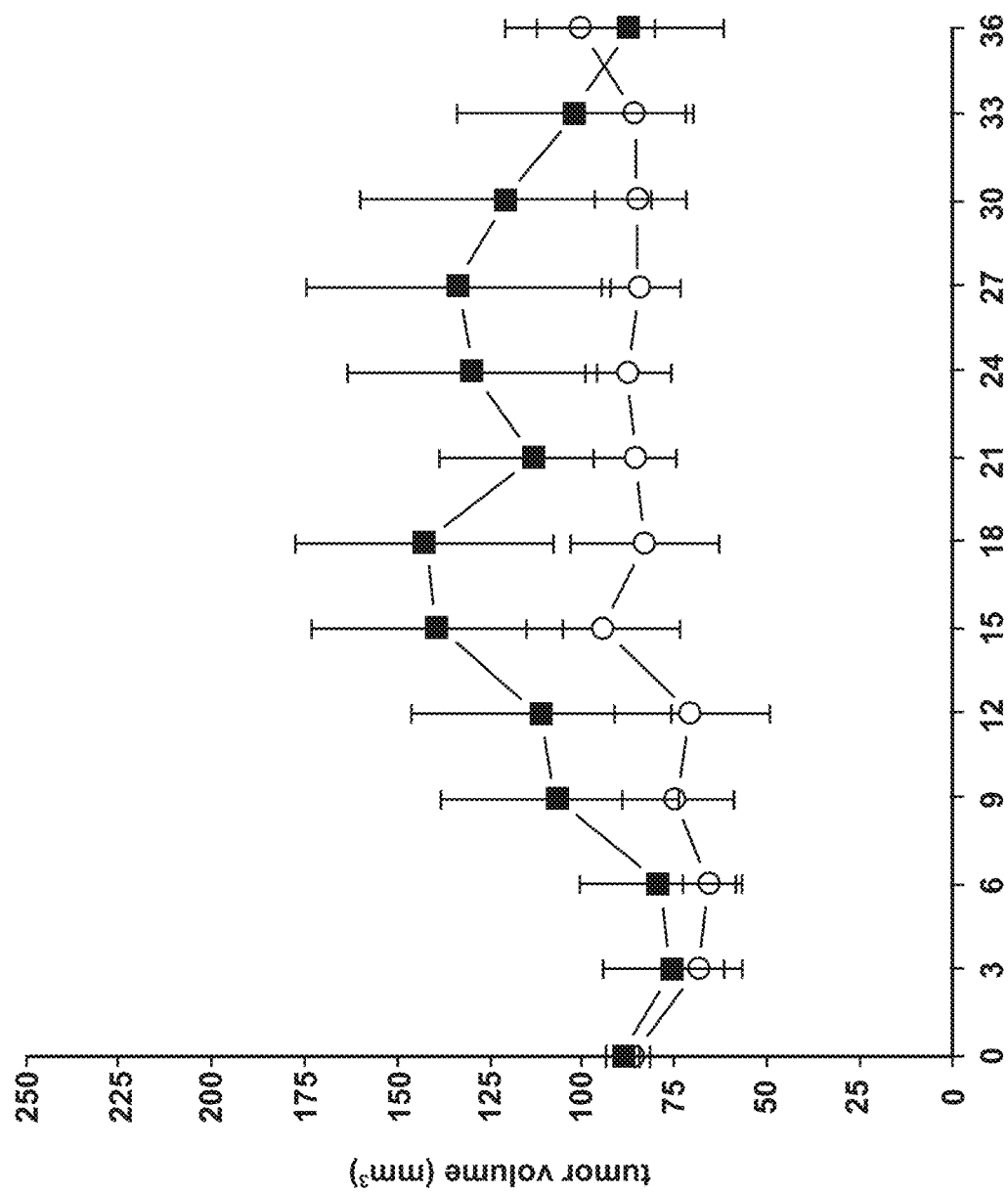
FIG. 2B is a graph illustrating average tumor volume in athymic nude mice xenografted with HCT 116 cells and treated with one embodiment of recombinant TPV (TPV/egfp) as compared to the vehicle-only control solution.

In the embodiment depicted in FIG. 2B, the black filled squares illustrate the average tumor volume of mice in group B, which were treated with TPV/egfp and the average tumor volume of mice in control group A. The bars illustrate the standard error of the mean (+/−1 SEM) for the tumor volume in control group A and the tumor volume in group B.

Figure 2C:
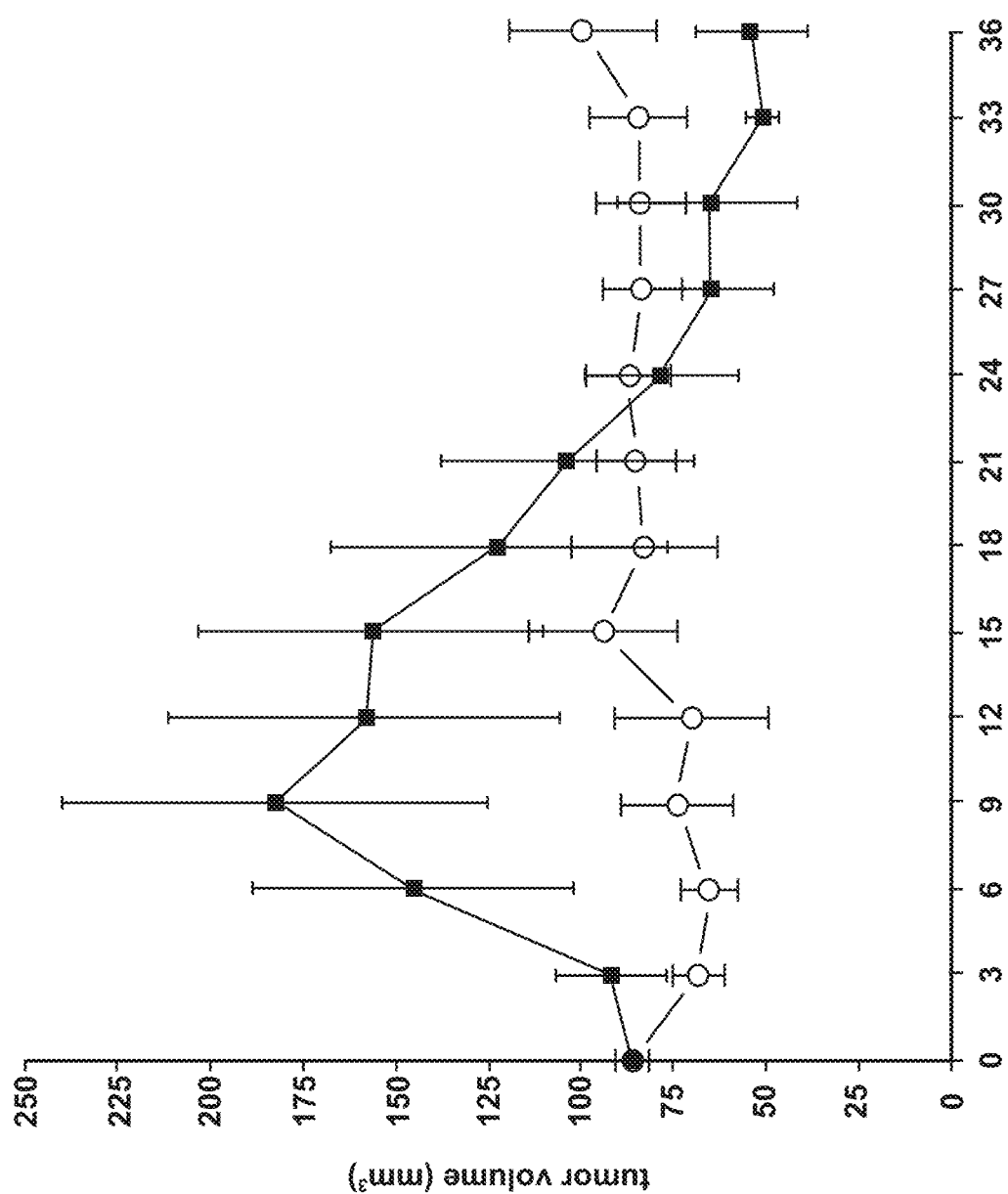
FIG. 2C is a graph illustrating average tumor volume in athymic nude mice xenografted with HCT 116 cells and treated with one embodiment of recombinant TPV (TPV-p2KO/Δ66R/mMCP-1) as compared to the vehicle-only control solution.

In the embodiment depicted in FIG. 2C, the black filled squares illustrate the average tumor volume of mice in group C which were treated with TPV-p2KO/Δ66R/mMCP-1 and the average tumor volume of mice in control group A. The bars illustrate the standard error of the mean (+/−1 SEM) for the tumor volume in control group A and the tumor volume in group C.

Figure 2D:
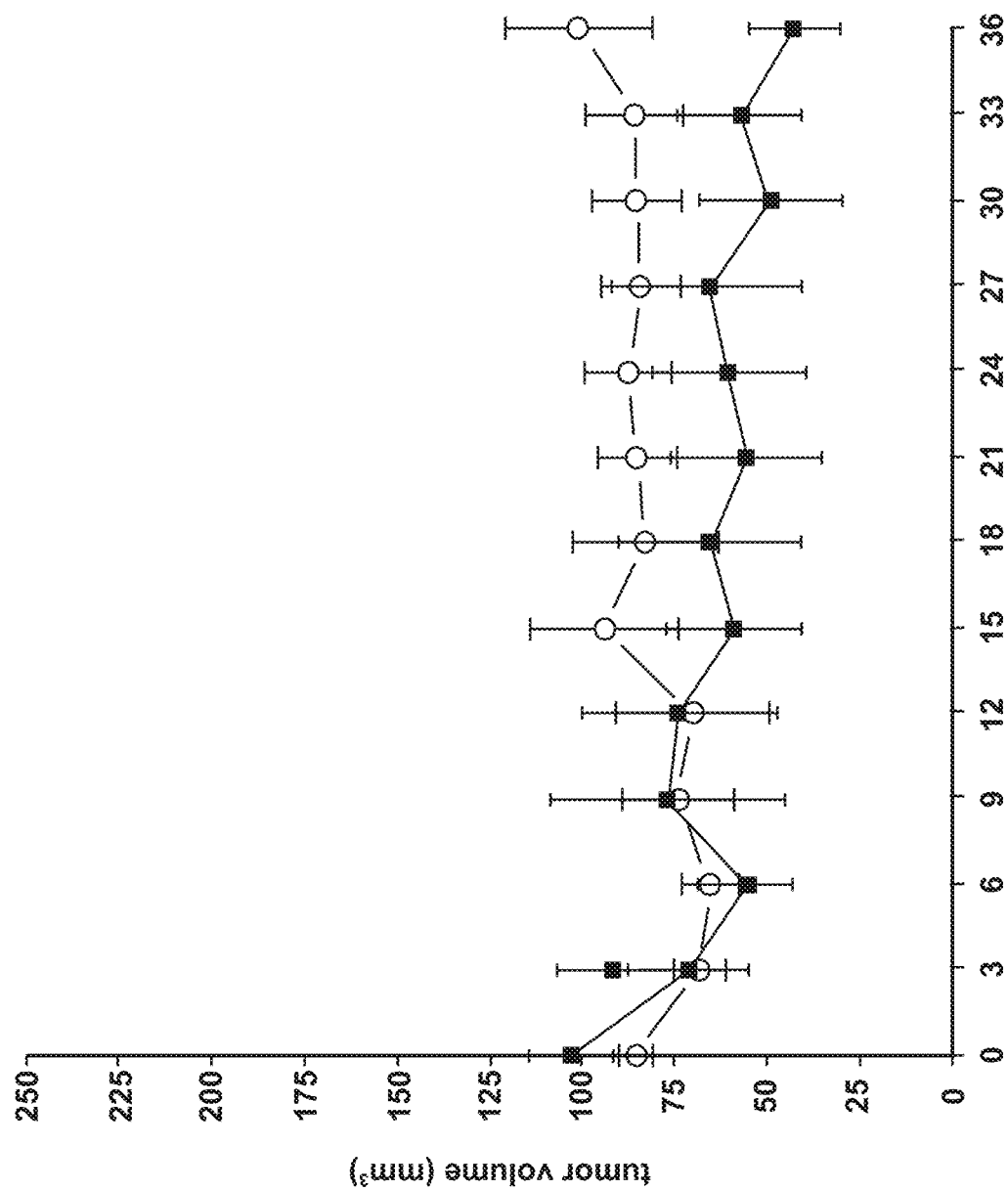
FIG. 2D is a graph illustrating average tumor volume in athymic nude mice xenografted with HCT 116 cells and treated with one embodiment of recombinant TPV (TPV-p2KO/Δ66R/mGM-CSF) as compared to the vehicle-only control solution.

In the embodiment depicted in FIG. 2D, the black filled squares illustrate the average tumor volume of mice in group D, which were treated with TPV-p2KO/Δ66R/mGM-CSF and the average tumor volume of mice in control group A. The bars illustrate the standard error of the mean (+/−1 SEM) for the tumor volume in control group A and the tumor volume in group D.

Figure 2E:
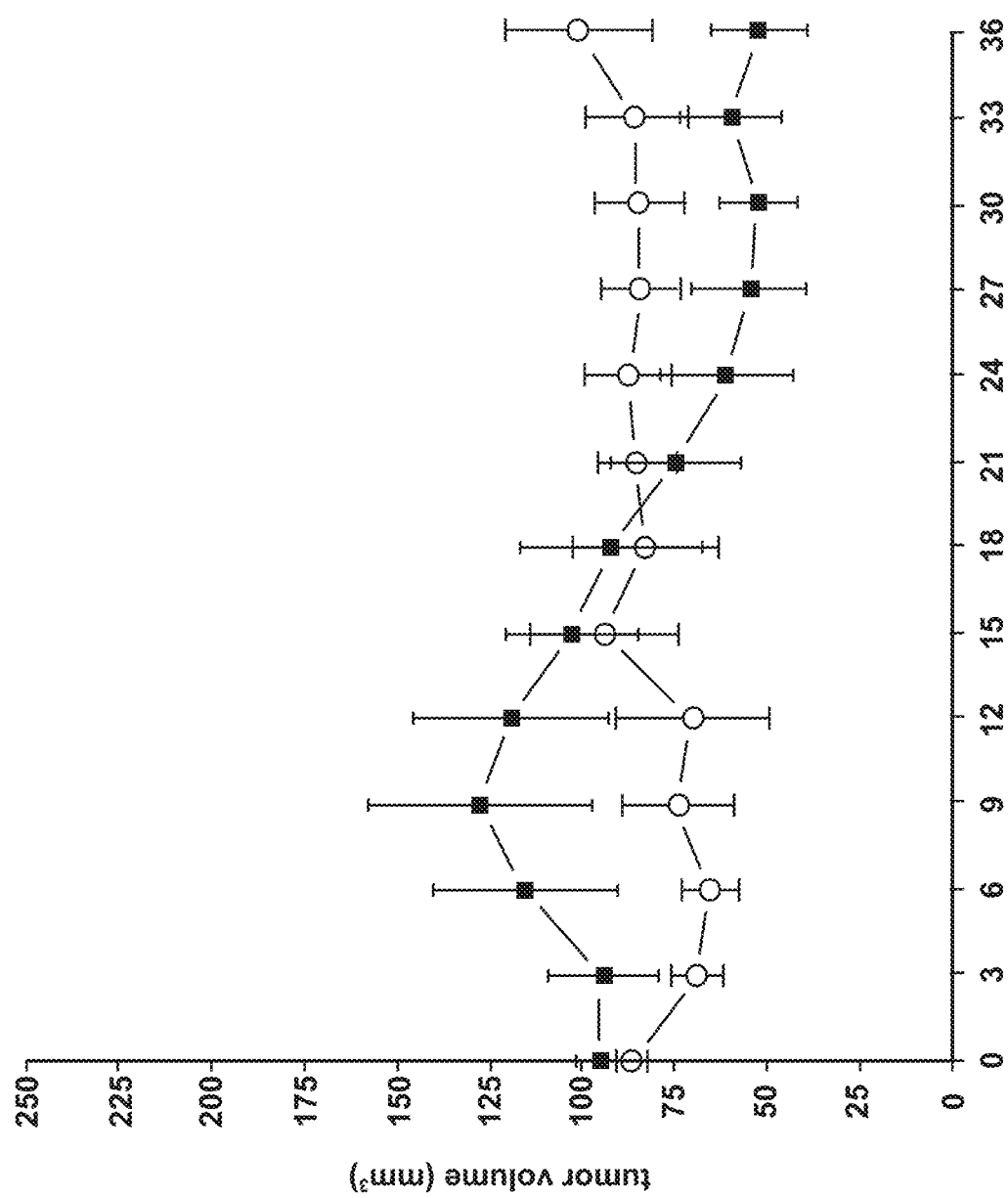
FIG. 2E is a graph illustrating average tumor volume in athymic nude mice xenografted with HCT 116 cells and treated with one embodiment of recombinant TPV (TPV-p2KO/Δ66R/fliC) as compared to the vehicle-only control solution.

In the embodiment depicted in FIG. 2E, the black filled squares illustrate the average tumor volume of mice in group E, which were treated with TPV-p2KO/Δ66R/fliC and the average tumor volume of mice in control group A. The bars illustrate the standard error of the mean (+/−1 SEM) for the tumor volume in control group A and the tumor volume in group E.

Figure 2F:
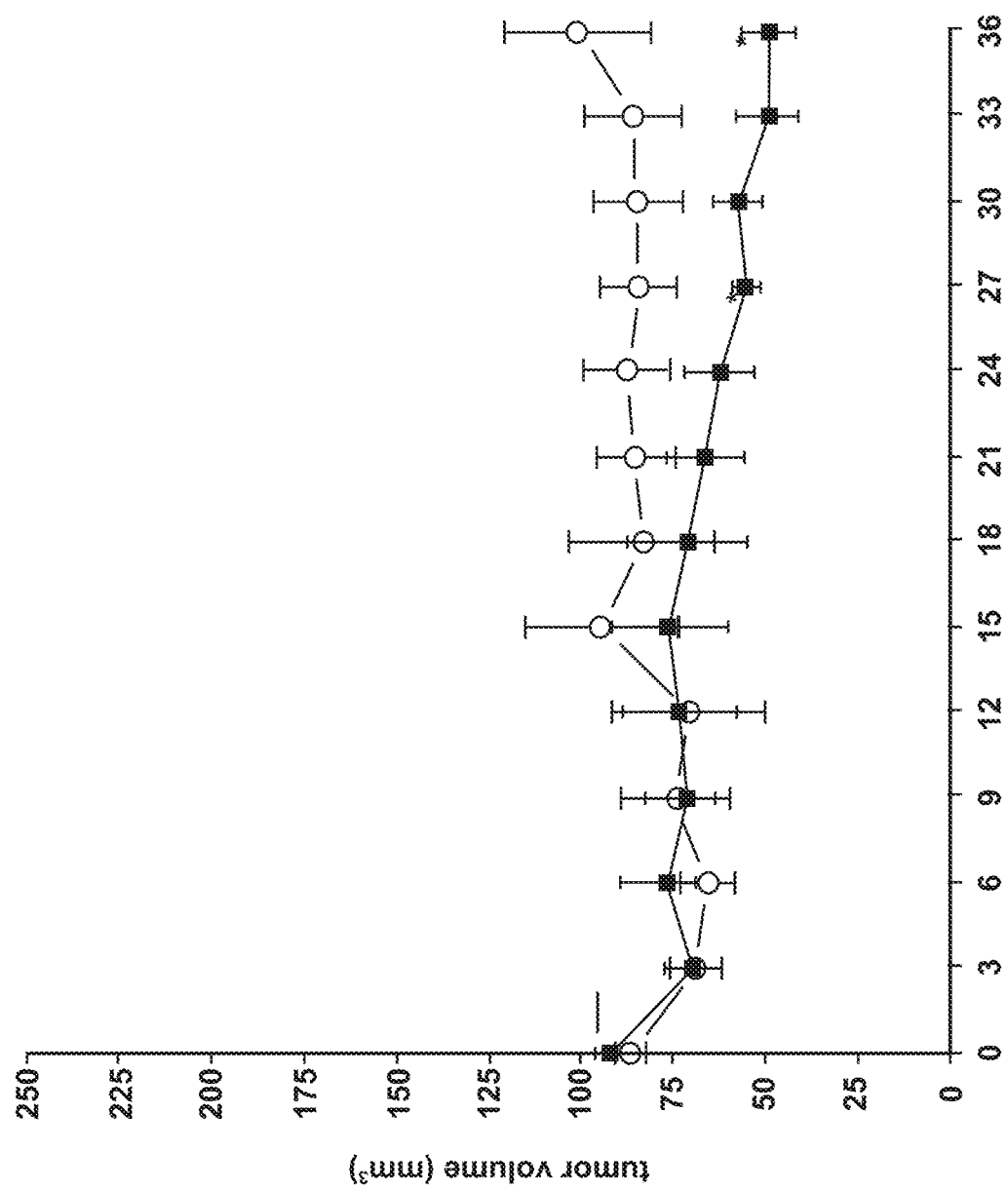
FIG. 2F is a graph illustrating average tumor volume in athymic nude mice xenografted with HCT 116 cells and treated with one embodiment of recombinant TPV (TPV-p2KO/Δ66R) as compared to the vehicle-only control solution.

In the embodiment depicted in FIG. 2F, the black filled squares illustrate the average tumor volume of mice in group F, which were treated with TPV-p2KO/Δ66R and the average tumor volume of mice in control group A. The bars illustrate the standard error of the mean (+/−1 SEM) for the tumor volume in control group A and the tumor volume in group F.

Figure 2G:
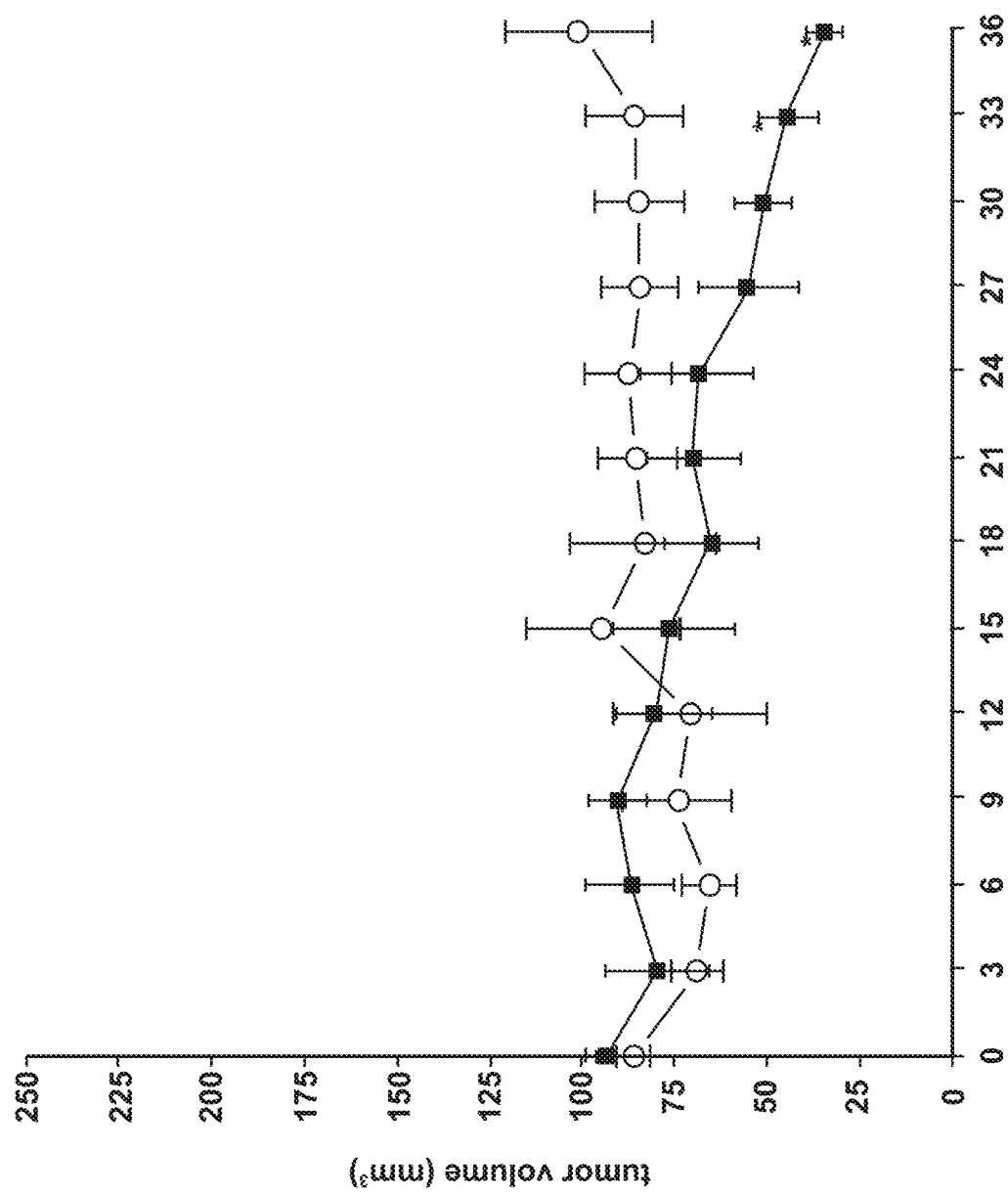
FIG. 2G is a graph illustrating average tumor volume in athymic nude mice xenografted with HCT 116 cells and treated with one embodiment of recombinant TPV (TPV-p2KO/Δ2L) as compared to the vehicle-only control solution.

In the embodiment depicted in FIG. 2G, the black filled squares illustrate the average tumor volume of mice in group G, which were treated with TPV-p2KO/Δ2L and the average tumor volume of mice in control group A. The bars illustrate the standard error of the mean (+/−1 SEM) for the tumor volume in control group A and the tumor volume in group G.

Figure 2H:
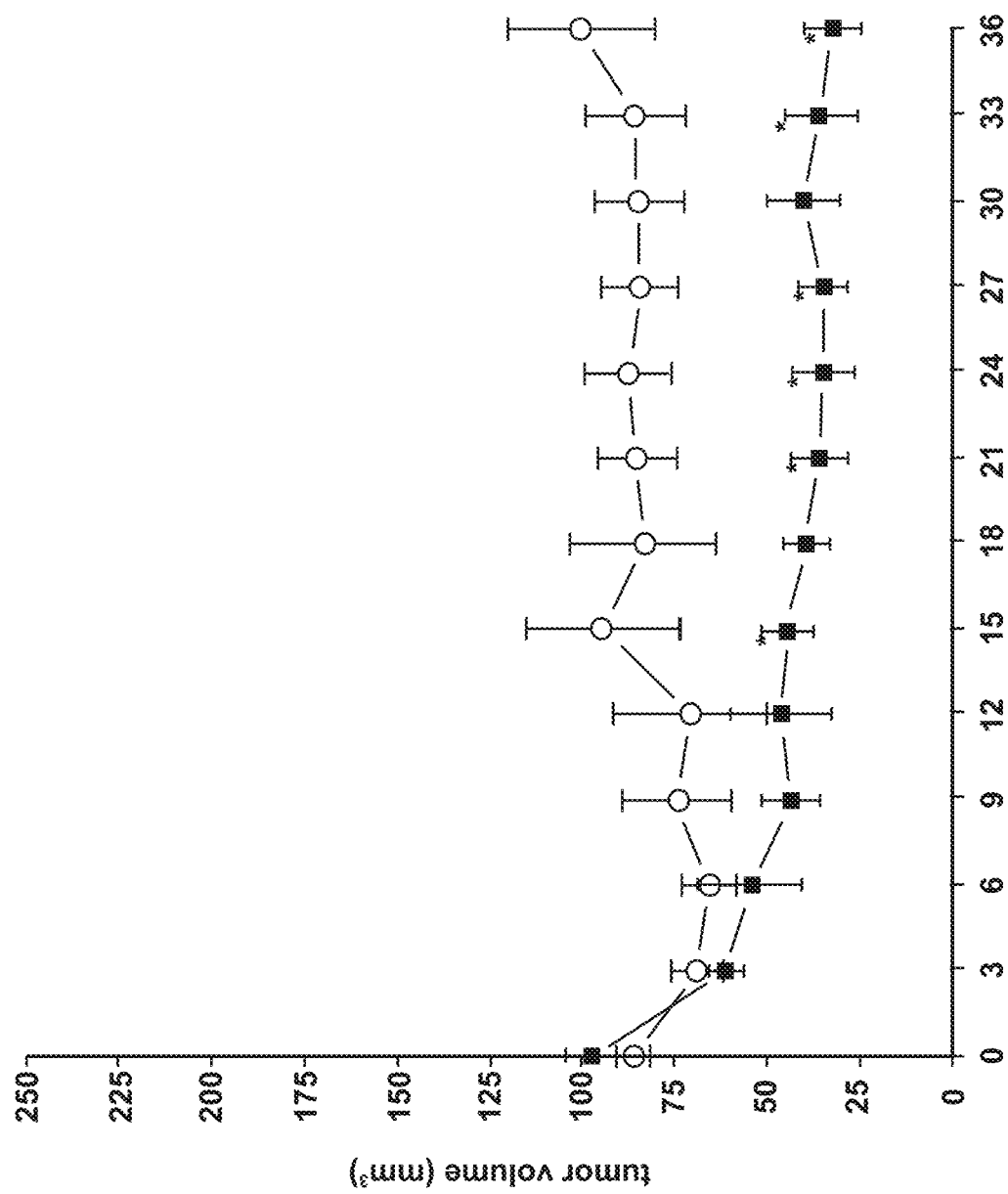
FIG. 2H is a graph illustrating average tumor volume in athymic nude mice xenografted with HCT 116 cells and treated with one embodiment of recombinant TPV (TPV-p2KO/Δ2L/Δ66R/fliC) as compared to the vehicle-only control solution.

In the embodiment depicted in FIG. 2H, the black filled squares illustrate the average tumor volume of mice in group H, which were treated with TPV-p2KO/Δ2L/Δ66R/fliC and the average tumor volume of mice in control group A. The bars illustrate the standard error of the mean (+/−1 SEM) for the tumor volume in control group A and the tumor volume in group H.

Referring to FIGS. 4A-4E, the effectiveness of mutant viruses in tumor suppression in melanoma tumor models is shown in vivo. Melanoma tumors were induced in 6-8 week old athymic nude mice by subcutaneously injecting 5×10$^6$ SK-MEL-3 cells onto the dorsal surface. Mice were randomly segregated into the control or experimental groups with each group containing five mice (n=5) when the tumor size reached 45±4.5 mm$^3$. Mice in the experimental groups were treated with intratumoral injections of 5×10$^6$ pfu of virus, while the mice in the mock group were intratumorally injected with medium only. Tumor volumes were measured using the digital calipers every day. In each graph shown here, the y-axis represents the average percentage of tumor growth (%) and the x-axis is time (days post virotherapeutic treatment). All experimental groups are compared to the mock group in which the mice were treated with only medium injection. Bars show the standard error of the mean (±1 SEM). Points indicated with an asterisk (*) refer to tumor growth that was significantly reduced from the control (P≤0.05). Asterisks were marked every 3 days if there was significance.

Figure 4A:
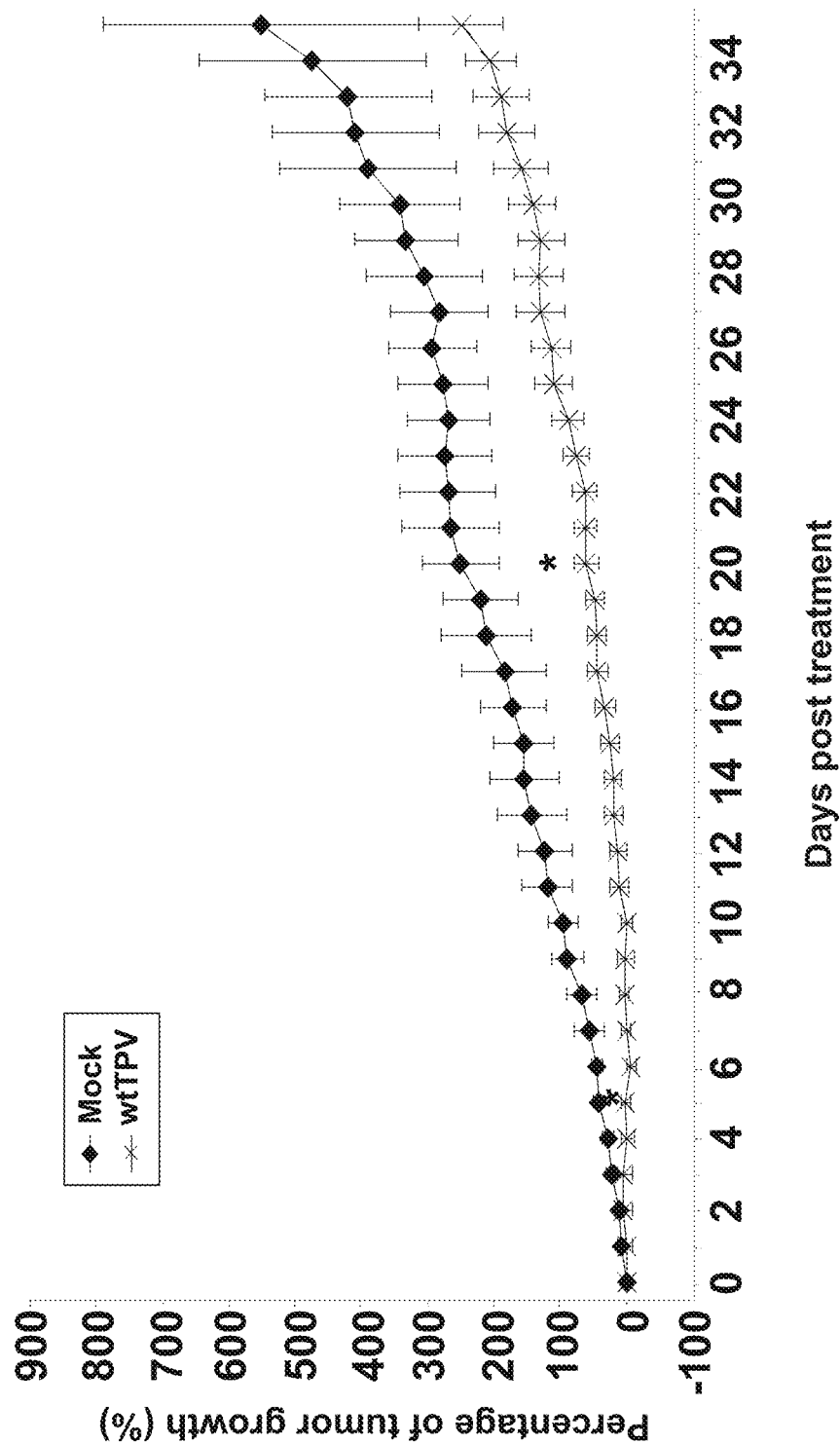
FIG. 4A is a graph illustrating average tumor volume in athymic nude mice xenografted with SK-MEL-3 cells and treated with a wild-type TPV (wtTPV) as compared to a vehicle-only solution.

In the embodiment depicted in FIG. 4A, the black X's illustrate the percentage of tumor growth of mice in group A, which were treated with wtTPV and the average tumor growth of mice in control group A. The bars illustrate the standard error of the mean (+/−1 SEM) for the tumor growth in control group A and the tumor growth in group A.

Figure 4B:
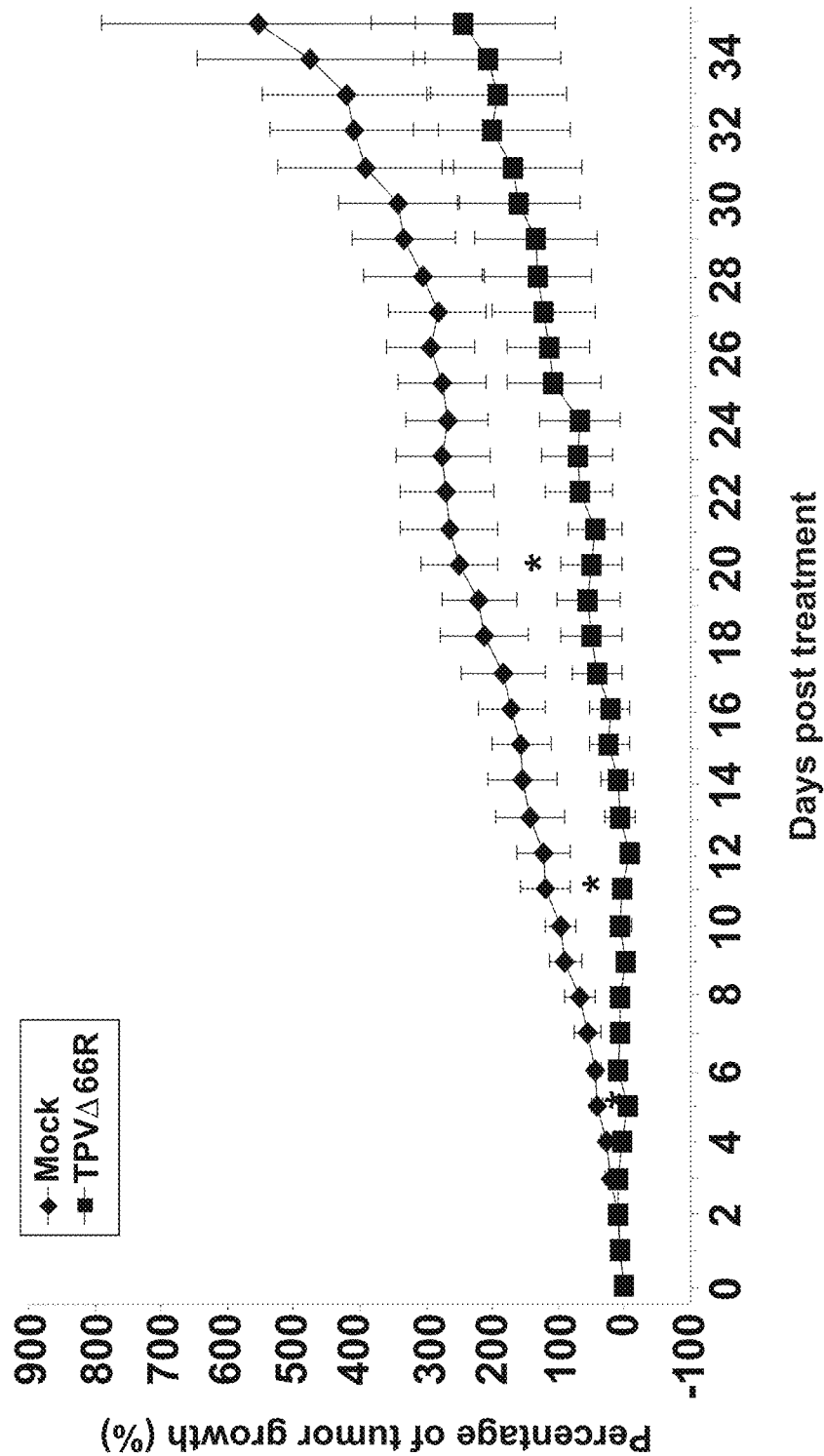
FIG. 4B is a graph illustrating average tumor volume in athymic nude mice xenografted with SK-MEL-3 cells and treated with one embodiment of recombinant TPV (TPV-p2KO/Δ66R) as compared to the vehicle-only solution.

In the embodiment depicted in FIG. 4B, the black filled squares illustrate the percentage of tumor growth of mice in group B, which were treated with TPV/p2KO/Δ66R and the percentage of tumor growth of mice in control group A. The bars illustrate the standard error of the mean (+/−1 SEM) for the tumor growth in control group A and the tumor growth in group B.

Figure 4C:
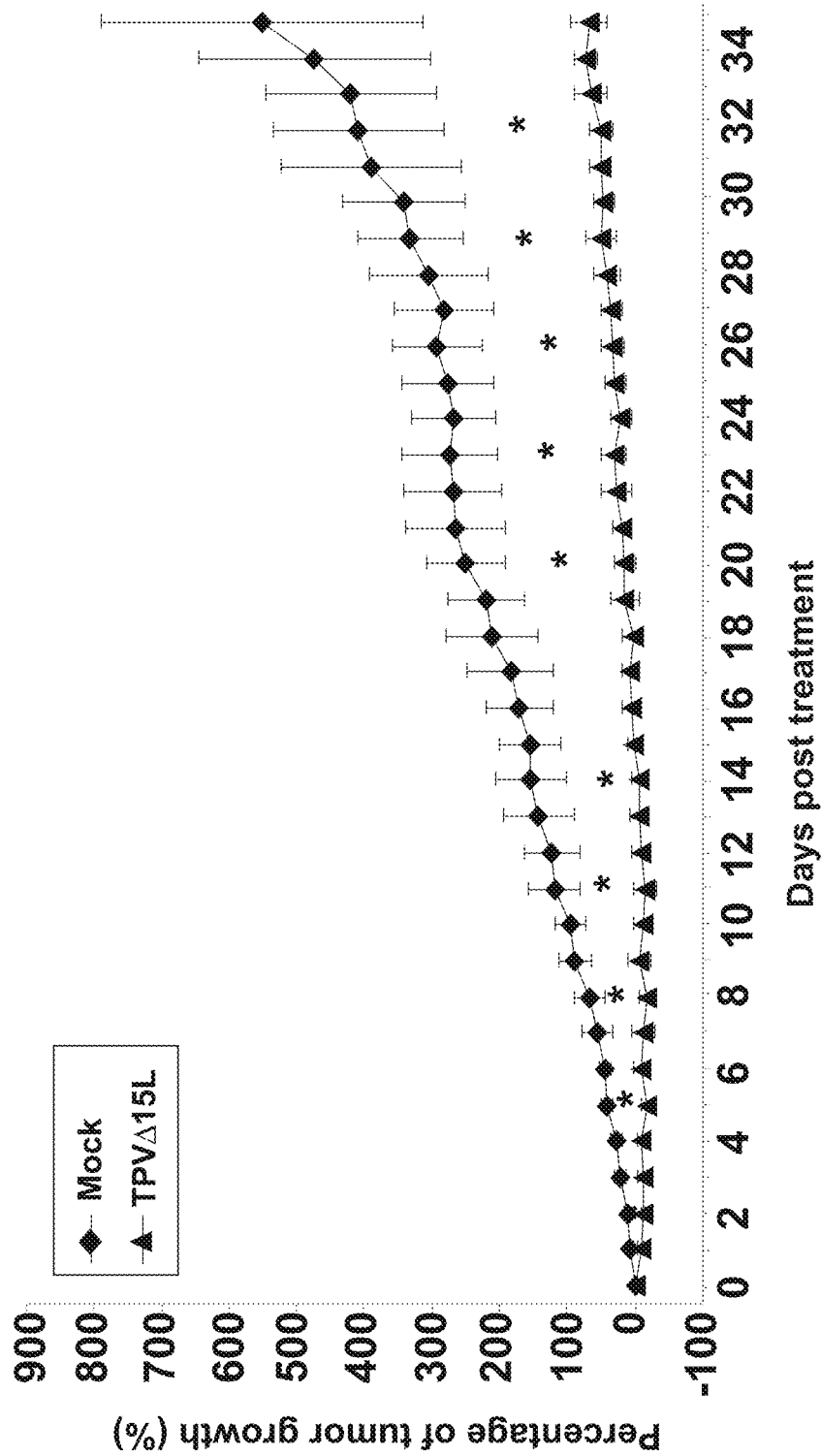
FIG. 4C is a graph illustrating average tumor volume in athymic nude mice xenografted with SK-MEL-3 cells and treated with one embodiment of recombinant TPV (TPV-p2KO/Δ15L) as compared to the vehicle-only solution.

In the embodiment depicted in FIG. 4C, the black filled squares illustrate the percentage of tumor growth of mice in group C which were treated with TPV-p2KO/Δ15L and the percentage of tumor growth of mice in control group A. The bars illustrate the standard error of the mean (+/−1 SEM) for the tumor growth in control group A and the tumor growth in group C.

Figure 4D:
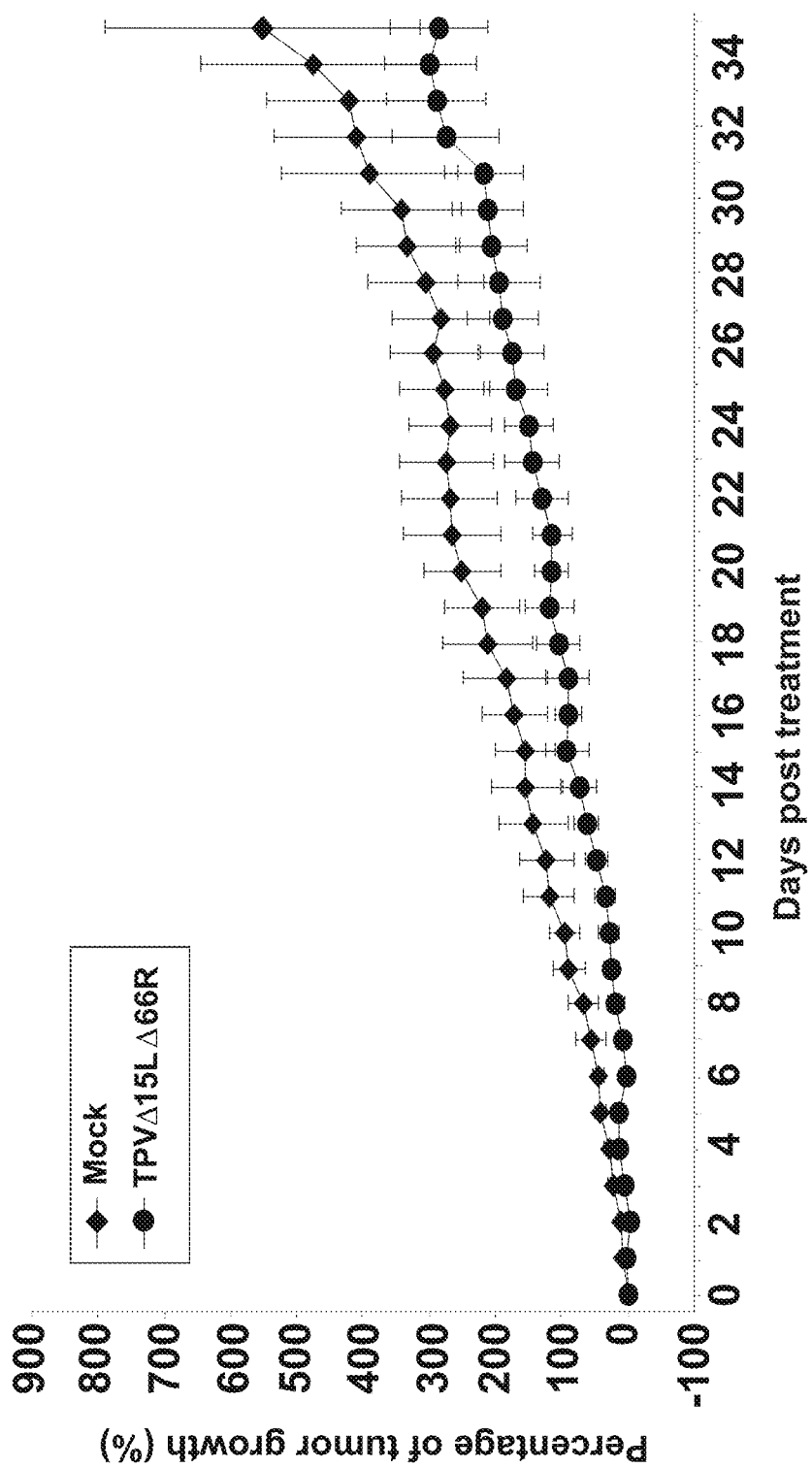
FIG. 4D is a graph illustrating average tumor volume in athymic nude mice xenografted with SK-MEL-3 cells and treated with one embodiment of recombinant TPV (TPV-p2KO/Δ15LΔ66R) as compared to the vehicle-only solution.

In the embodiment depicted in FIG. 4D, the black filled squares illustrate the percentage of tumor growth of mice in group D, which were treated with TPV-p2KO/Δ15LΔ66R and the percentage of tumor growth of mice in control group A. The bars illustrate the standard error of the mean (+/−1 SEM) for the tumor growth in control group A and the tumor growth in group D.

Figure 4E:
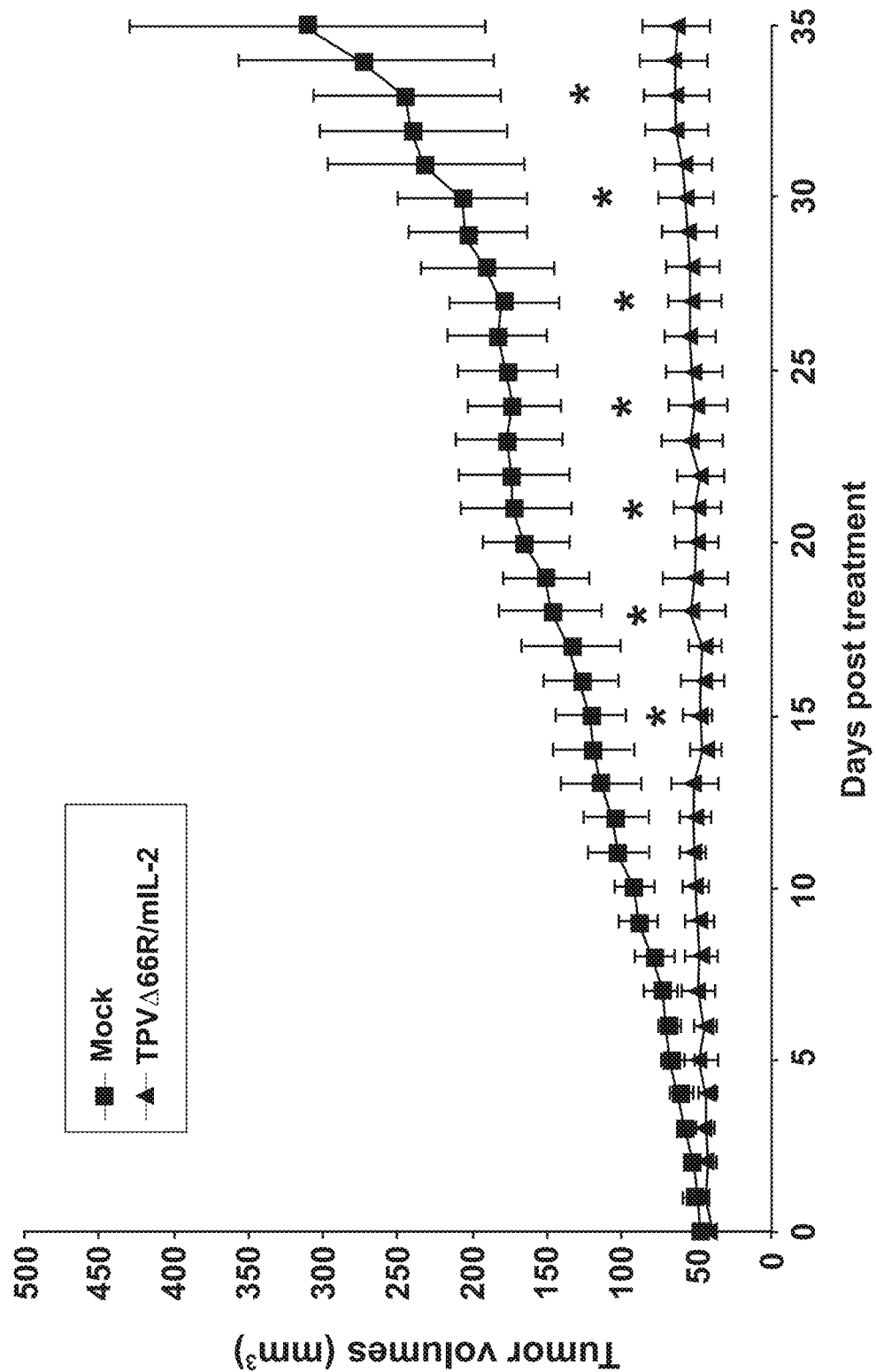
FIG. 4E is a graph illustrating average tumor volume in athymic nude mice xenografted with SK-MEL-3 cells and treated with one embodiment of recombinant TPV (TPV-p2KO/Δ66R/mIL-2) as compared to the vehicle-only solution.

In the embodiment depicted in FIG. 4E, the black filled squares illustrate the average tumor volume of mice in group E, which were treated with TPV-p2KO/Δ66R/mIL-2 and the average tumor volume of mice in control group A. The bars illustrate the standard error of the mean (+/−1 SEM) for the tumor volume in control group A and the tumor volume in group E.

Referring to FIGS. 5A-5J, effectiveness of mutant viruses in tumor suppression in melanoma tumor models in vivo. Melanoma tumors were induced in 6-8 week old athymic nude mice by subcutaneously injecting 5×10$^6$ MDA-MB-231 cells onto the dorsal surface. Mice were randomly segregated into the control or experimental groups with each group containing five mice (n=5) when the tumor size reached 45±4.5 mm$^3$. Mice in the experimental groups were treated with intratumoral injections of 5×10$^6$ pfu of virus, while the mice in the mock group were intratumorally injected with medium only. Tumor volumes were measured using the digital calipers every day. In each graph shown here, the y-axis represents the average percentage of tumor growth (%) and the x-axis is time (days post virotherapeutic treatment). All experimental groups are compared to the mock group in which the mice were treated with only medium injection. Bars show the standard error of the mean (±1 SEM). Points indicated with an asterisk (*) refer to tumor growth that was significantly reduced from the control (P≤0.05). Asterisks were marked every 3 days if there was significance.

In the embodiment depicted in FIG. 5A, the black filled squares illustrate the average tumor volume of mice in group A, which were treated with wtTPV and the average tumor volume of mice in control group A. The bars illustrate the standard error of the mean (+/−1 SEM) for the tumor volume in control group A and the tumor volume in group A.

Figure 5B:
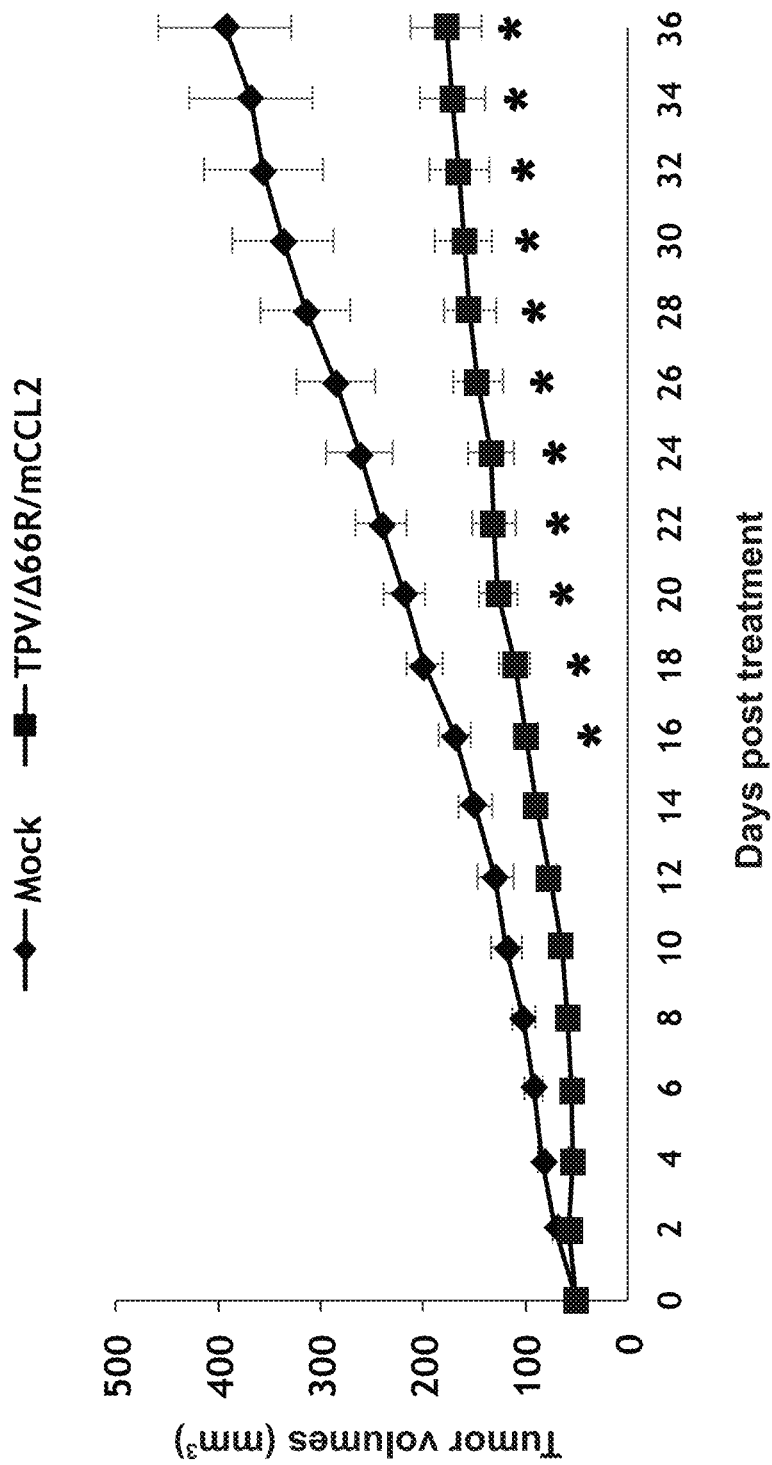
FIG. 5B is a graph illustrating average tumor volume in athymic nude mice xenografted with MDA-MB-231 cells and treated with one embodiment of recombinant TPV (TPV-p2KO/Δ66R/mCCL2) as compared to the vehicle-only solution.

In the embodiment depicted in FIG. 5B, the black filled squares illustrate the average tumor volume of mice in group B, which were treated with TPV-p2KO/Δ66R/mCCL2 and the average tumor volume of mice in control group A. The bars illustrate the standard error of the mean (+/−1 SEM) for the tumor volume in control group A and the tumor volume in group B.

Figure 5C:
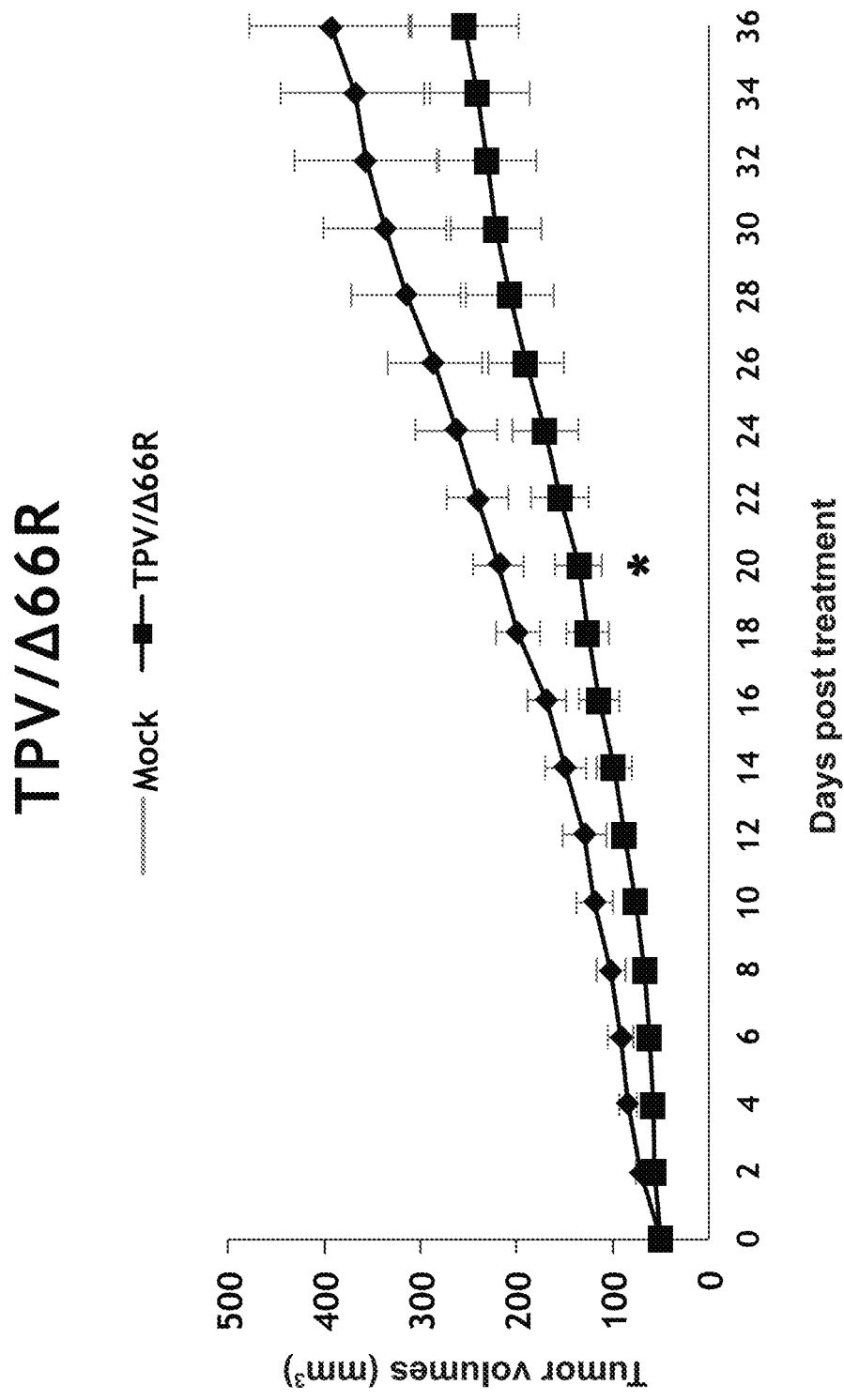
FIG. 5C is a graph illustrating average tumor volume in athymic nude mice xenografted with MDA-MB-231 cells and treated with one embodiment of recombinant TPV (TPV-p2KO/Δ66R) as compared to the vehicle-only solution.

In the embodiment depicted in FIG. 5C, the black filled squares illustrate the average tumor volume of mice in group C which were treated with TPV-p2KO/Δ66R and the average tumor volume of mice in control group A. The bars illustrate the standard error of the mean (+/−1 SEM) for the tumor volume in control group A and the tumor volume in group C.

In the embodiment depicted in FIG. 5D, the black filled squares illustrate the average tumor volume of mice in group D, which were treated with TPV-p2KO/Δ66R/mIL2 and the average tumor volume of mice in control group A. The bars illustrate the standard error of the mean (+/−1 SEM) for the tumor volume in control group A and the tumor volume in group D.

Figure 5E:
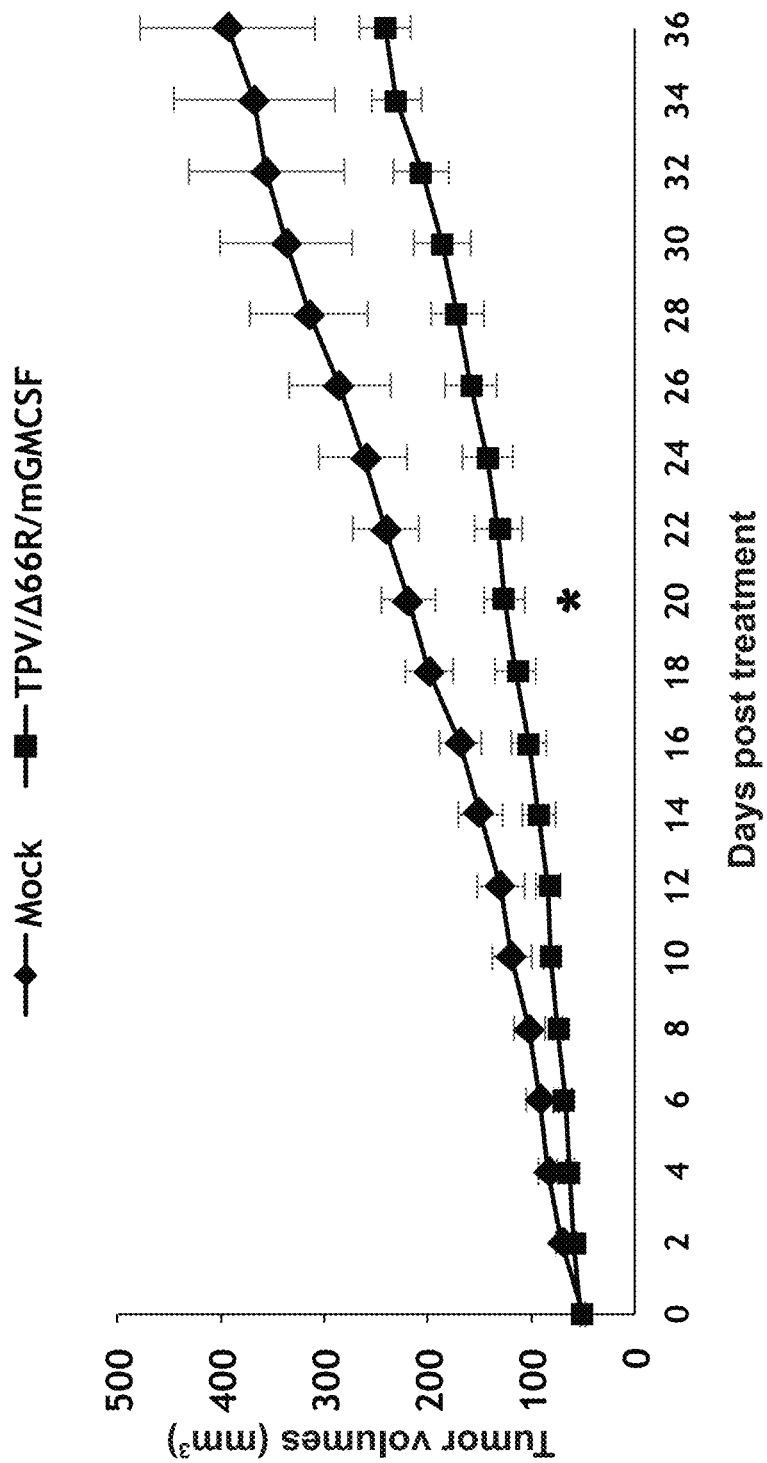
FIG. 5E is a graph illustrating average tumor volume in athymic nude mice xenografted with MDA-MB-231 cells and treated with one embodiment of recombinant TPV (TPV-p2KO/Δ66R/mGMCSF) as compared to the vehicle-only solution.

In the embodiment depicted in FIG. 5E, the black filled squares illustrate the average tumor volume of mice in group E, which were treated with TPV-p2KO/Δ66R/mGMCSF and the average tumor volume of mice in control group A. The bars illustrate the standard error of the mean (+/−1 SEM) for the tumor volume in control group A and the tumor volume in group E.

Figure 5F:
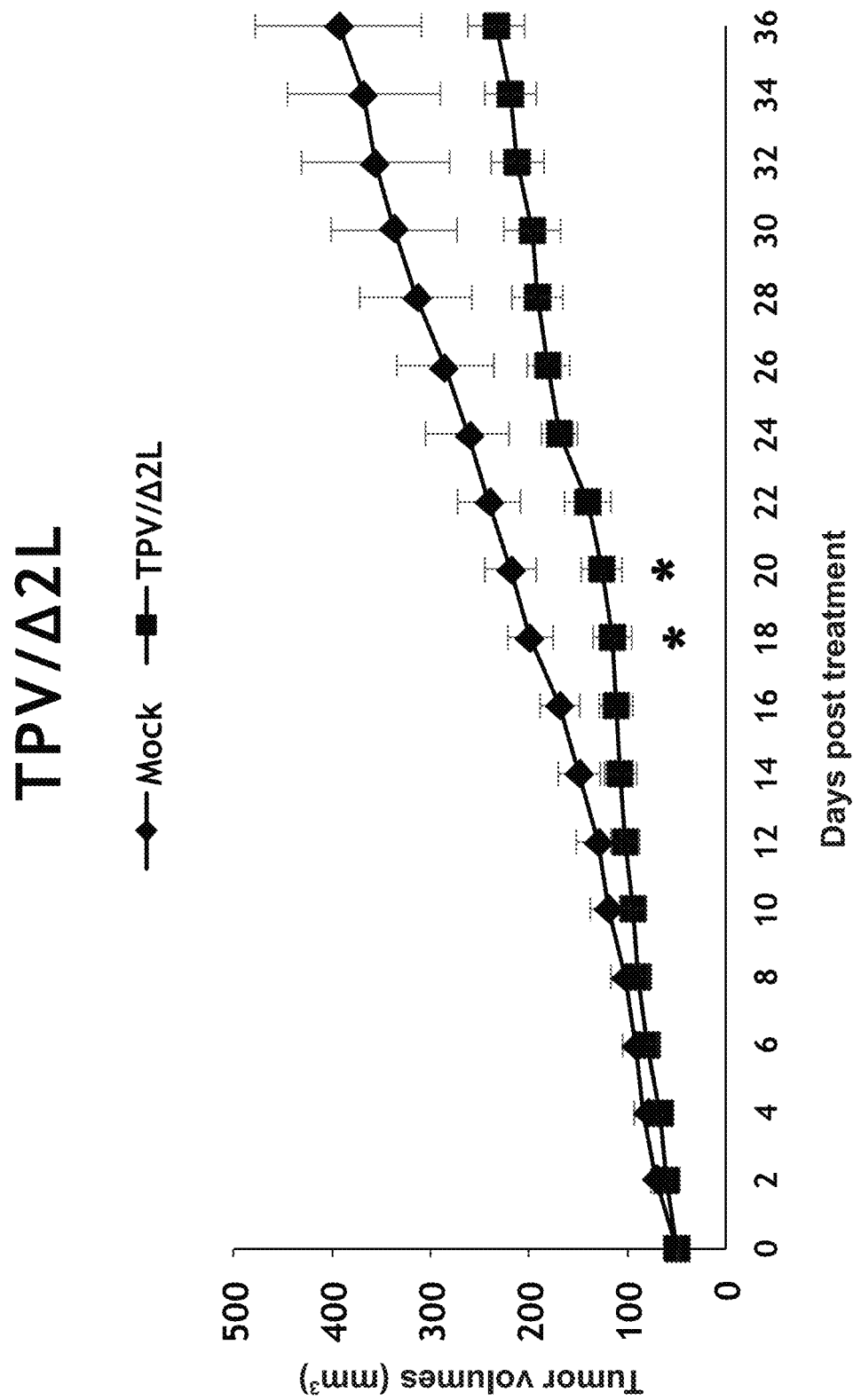
FIG. 5F is a graph illustrating average tumor volume in athymic nude mice xenografted with MDA-MB-231 cells and treated with one embodiment of recombinant TPV (TPV-p2KO/Δ2L) as compared to the vehicle-only solution.

In the embodiment depicted in FIG. 5F, the black filled squares illustrate the average tumor volume of mice in group F, which were treated with TPV-p2KO/Δ2L and the average tumor volume of mice in control group A. The bars illustrate the standard error of the mean (+/−1 SEM) for the tumor volume in control group A and the tumor volume in group F.

In the embodiment depicted in FIG. 5G, the black filled squares illustrate the average tumor volume of mice in group G, which were treated with TPV-p2KO/Δ66R/FliC and the average tumor volume of mice in control group A. The bars illustrate the standard error of the mean (+/−1 SEM) for the tumor volume in control group A and the tumor volume in group G.

Figure 5H:
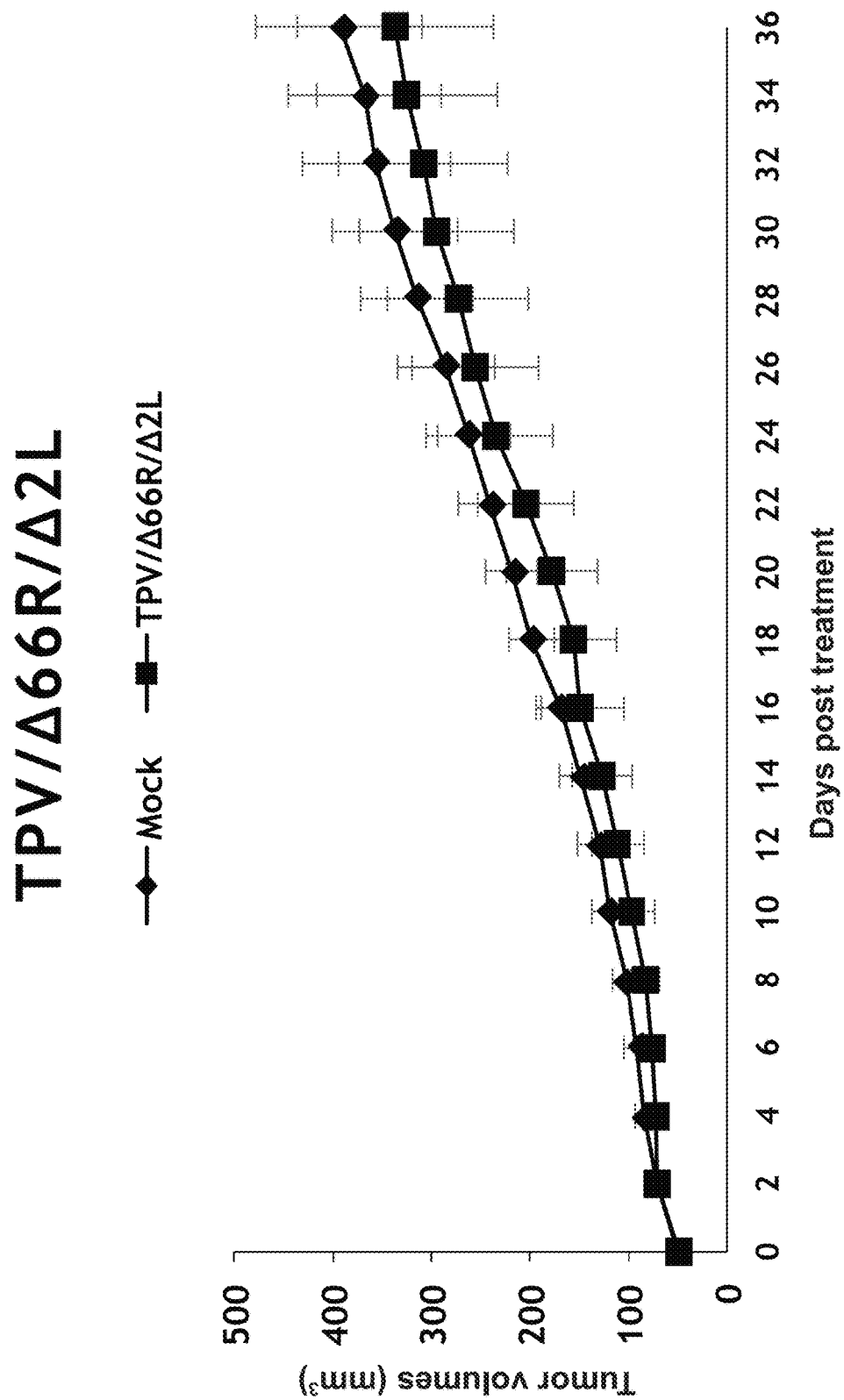
FIG. 5H is a graph illustrating average tumor volume in athymic nude mice xenografted with MDA-MB-231 cells and treated with one embodiment of recombinant TPV (TPV-p2KO/Δ66R/Δ2L) as compared to the vehicle-only solution.

In the embodiment depicted in FIG. 5H, the black filled squares illustrate the average tumor volume of mice in group H, which were treated with TPV-p2KO/Δ66R/Δ2L and the average tumor volume of mice in control group A. The bars illustrate the standard error of the mean (+/−1 SEM) for the tumor volume in control group A and the tumor volume in group H.

Figure 5I:
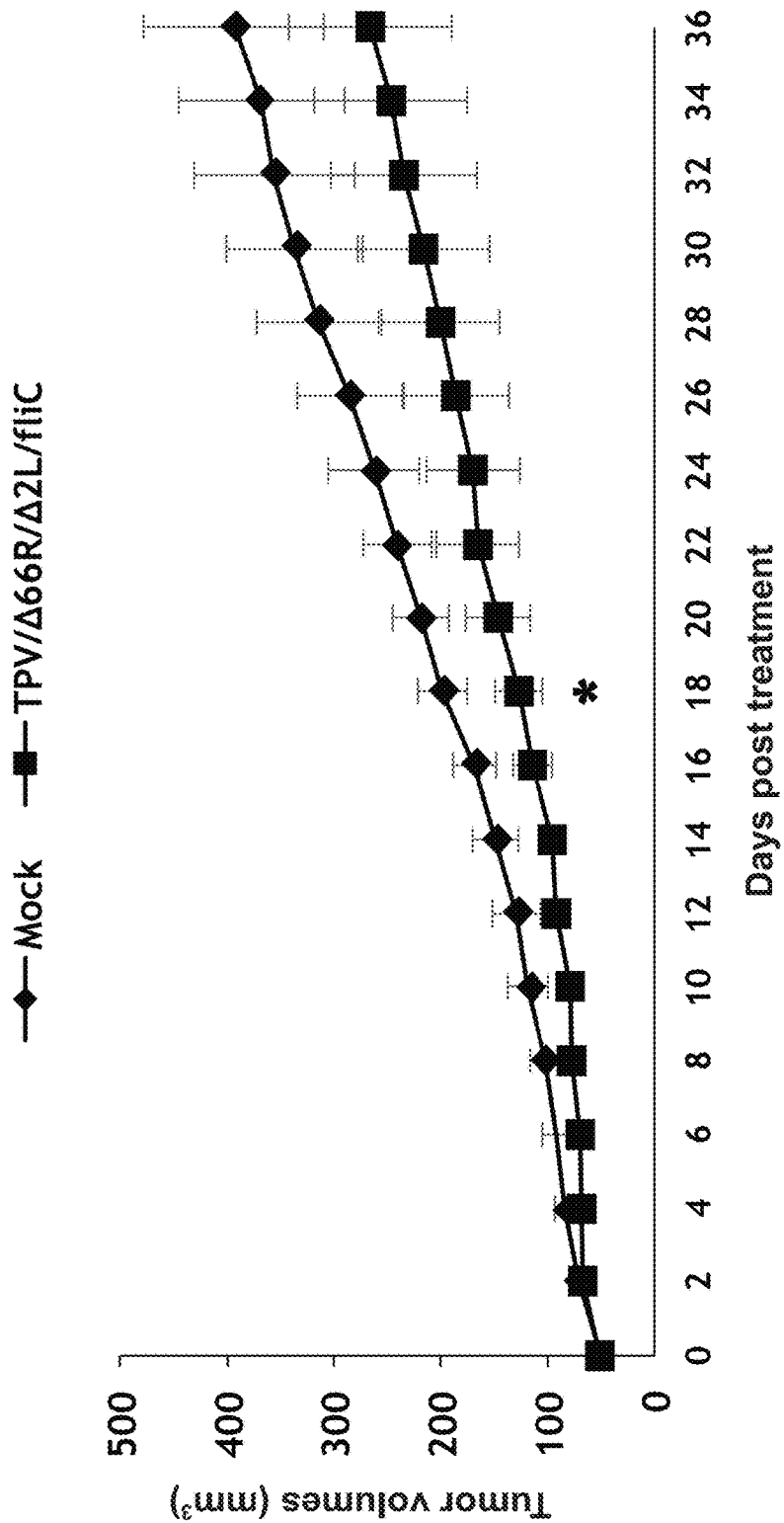
FIG. 5I is a graph illustrating average tumor volume in athymic nude mice xenografted with MDA-MB-231 cells and treated with one embodiment of recombinant TPV (TPV-p2KO/Δ66R/Δ2L/FliC) as compared to the vehicle-only solution.

In the embodiment depicted in FIG. 5I, the black filled squares illustrate the average tumor volume of mice in group I, which were treated with TPV-p2KO/Δ66R/Δ2L/FliC and the average tumor volume of mice in control group A. The bars illustrate the standard error of the mean (+/−1 SEM) for the tumor volume in control group A and the tumor volume in group I.

Figure 5J:
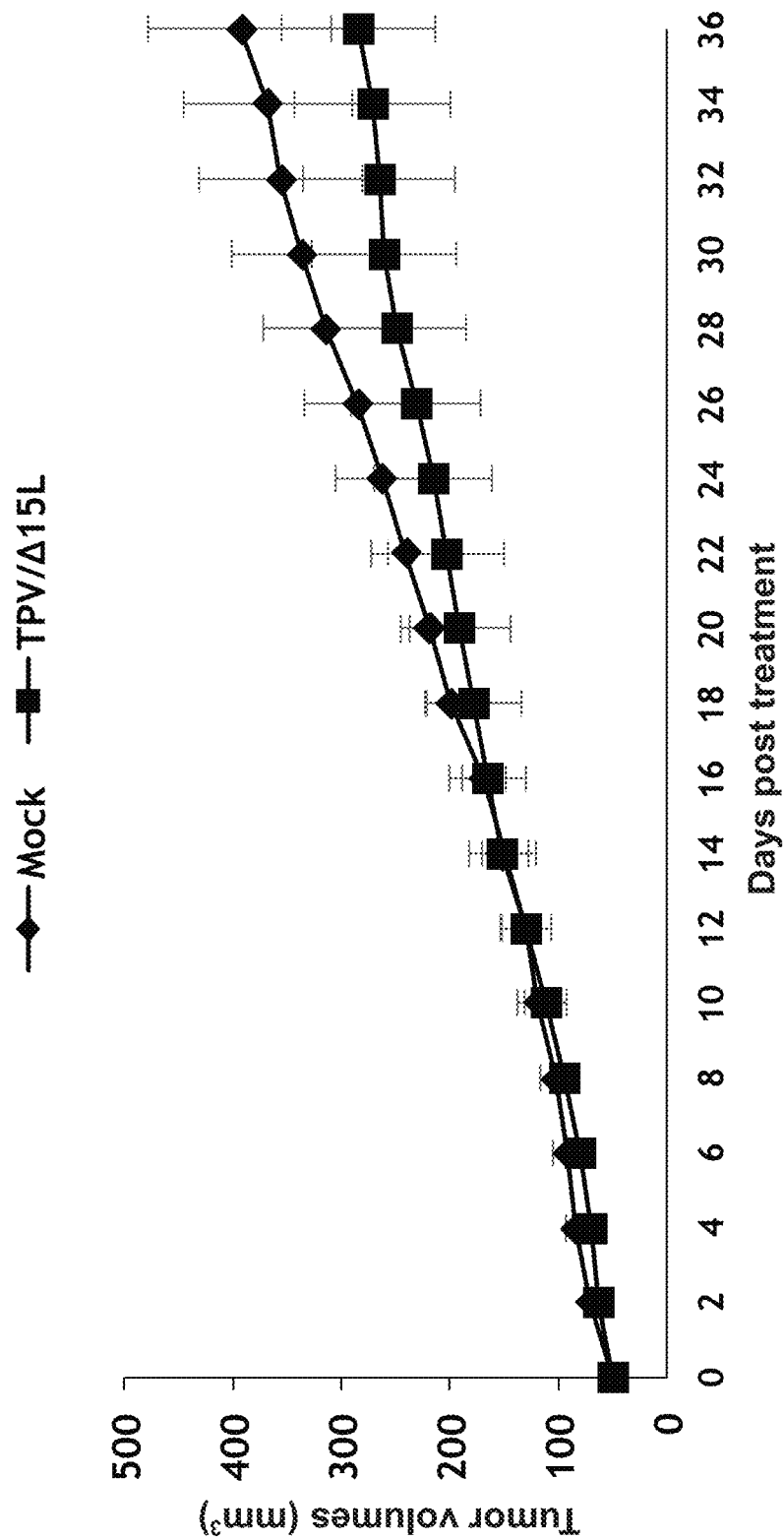
FIG. 5J is a graph illustrating average tumor volume in athymic nude mice xenografted with MDA-MB-231 cells and treated with one embodiment of recombinant TPV (TPV-p2KO/Δ15L) as compared to the vehicle-only solution.

In the embodiment depicted in FIG. 5J, the black filled squares illustrate the average tumor volume of mice in group J, which were treated with TPV-p2KO/Δ15L and the average tumor volume of mice in control group A. The bars illustrate the standard error of the mean (+/−1 SEM) for the tumor volume in control group A and the tumor volume in group J.

One particularly preferred embodiment of the recombinant TPV for use herein is a recombinant TPV with the fliC transgene added to a double-knockout background (Δ66R and Δ2L). Our results demonstrate that the recombinant TPV deleted for both 2L and 66R which expressed the fliC transgene produced a robust and durable therapeutic effect upon HCT 116 tumor xenografts. Another preferred embodiment of the recombinant TPV for use herein is a recombinant TPV with the fliC transgene added to a single-knockout virus (Δ66R). Both of the single knockout recombinant TPV embodiments (TPV-p2KO/Δ66R and TPV-p2KO/Δ2L) showed statistically significant reductions in tumor volume at at least two time points, and in each case the observed significant reduction in tumor volume was temporally distant from the point of virotherapeutic inoculation. Both single knockout recombinant TPVs appeared to trend towards an effect at these later time points. Indeed, with the exception of the TPV/egfp virus, all embodiments of the recombinant TPVs tested appeared to produce some degree of tumor ablation, with the recombinant TPVs mentioned above being preferred. Since the T cell-dependent adaptive immune response is severely impaired in nude mice, the examples described herein demonstrate that the innate immune response is potentially capable of reducing the tumor burden in subjects and therefore recombinant TPV armed with an innate immune response activator is expected to be useful in subjects with immunodeficiency syndromes. We therefore conclude that OVs armed with activators of the innate immune response will also be useful in individuals with immunodeficiency syndromes.

As a highly-conserved pathogen-associated molecular pattern (PAMP), flagellins are targets for detector molecules involved in cytosolic immunosurveillance. For example, detection of flagellin by the Nod-like receptor NCLR4 (also known as Ipaf) triggers activation of the Ipaf inflammasome which in turn activates caspase-1 and maturation of the cytokine interleukin 1β (IL-1β) in macrophages. Although the expected amount of FliC produced in the course of an OV infection is expected to be small, in mice even minute amounts of bacterial flagellin (≤5 g/animal) administered by tail vein injection cause global (i.e., in both organs and plasma) elevations of the cytokines TNF, IL-1β, IL-6, and the chemokine MIP-2 (IL-8), as well as changes in the MEK intracellular signaling pathway. The action of FliC in mammalian cells is therefore partially independent of the TLR-based PAMP detectors, and has not yet been fully elucidated. However, based on the results described herein, the activation of the innate immune response by recombinant TPV expressing FliC appears to contribute to the reduction of tumor mass in nude mice, which have an intact innate immune response.

As represented in Table 2, the description herein, and the FIGS., each of the TPV recombinants may be represented with or without the p2KO designation. For example, TPV-p2KO/Δ66R may also be equally designated herein as TPV/Δ66R. The p2KO method described herein for ablation/insertion is not meant to be limiting and it is understood that any method known for ablating genes from the genome or inserting transgenes into the genome can be used to form the TPV recombinants. As described in the examples and detailed description, any of the genes provided herein may be ablated and/or added to the TPV genome in any order. For example, poxviruses, particularly poxviruses in the *Yatapoxvirus* genus, may have the 66R, 2L, and/or 15L gene ablated; in addition, may also have, for example, the mGM-CSF, mMCP-1, fliC, mIL-2, mCCL2, and/or mGMCSF transgene added. Any combination of the genes described herein may be ablated and/or added to the desired TPV recombinant. In some embodiments, skin cancers or melanomas may be treated as described herein with wt-TPV, TPV/Δ66R, TPV/Δ66R/mGMCSF, TPV/Δ15L, TPV/Δ66R/Δ15, TPV/Δ66R/mIL-2, and/or combinations thereof. In other embodiments, breast cancers may be treated as described herein with wt-TPV, TPV/Δ66R, TPV/Δ2L, TPV/Δ66R/Δ2L, TPV/Δ66R/FliC, TPV/Δ66R/Δ2L/FliC, TPV/Δ66R/mGMCSF, TPV/Δ66R/mCCL2(mMCP1), TPV/Δ15L, TPV/Δ66R/Δ15, TPV/Δ66R/mIL-2, and/or combinations thereof. In yet other embodiments, colorectal cancers may be treated as described herein with TPV/Δ66R, TPV/Δ2L, TPV/Δ66R/Δ2L, TPV/Δ66R/FliC, TPV/Δ66R/Δ2L/FliC, TPV/Δ66R/mGMCSF, TPV/Δ66R/mCCL2(mMCP1), and/or combinations thereof.

LIST OF NON-LIMITING EMBODIMENTS

Embodiment A is a composition for treating cancerous cells in a subject having an immune system, comprising: a virus in the *Yatapoxvirus* genus having at least one mutation, wherein the at least one mutation results in suppressed expression of a TNF binding protein by the virus.

The composition of Embodiment A wherein the virus to suppress expression of the TNF binding protein has a structure capable of binding to an MHC-1 light chain.

The composition of Embodiment A or Embodiment A with one or more of the intervening features wherein the virus is a *yatapoxvirus* which encodes a transgene expressing a bacterial flaggelin protein.

The composition of Embodiment A or Embodiment A with one or more of the intervening features wherein a polymerized flaggellin protein is the main component of the bacterial flagellin.

The composition of Embodiment A or Embodiment A with one or more of the intervening features wherein the transgene is a product of the *Salmonella enteric serovar typhimurium* gene ("fliC").

The composition of Embodiment A or Embodiment A with one or more of the intervening features wherein the virus is a tanapoxvirus (TPV), and wherein the at least one mutation suppresses expression of the TNF binding protein encoded by a 2L gene of the TPV.

The composition of Embodiment A or Embodiment A with one or more of the intervening features wherein the virus has a second mutation, and wherein a second mutation results in suppressed expression of thymidine kinase by the virus.

The composition of Embodiment A or Embodiment A with one or more of the intervening features wherein the virus is a tanapoxvirus (TPV), and wherein a second mutation suppresses expression of thymidine kinase encoded by a 66R gene of the TPV.

The composition of Embodiment A or Embodiment A with one or more of the intervening features wherein the virus further encodes a transgene to increase apoptosis of the cancerous cells.

The composition of Embodiment A or Embodiment A with one or more of the intervening features wherein the virus further encodes a transgene to activate the immune system of the subject.

The composition of Embodiment A or Embodiment A with one or more of the intervening features wherein the virus further encodes a transgene to introduce a mCherry fluorescent reporter.

The composition of Embodiment A or Embodiment A with one or more of the intervening features wherein the virus further encodes a transgene to introduce a green fluorescent protein fluorescent reporter.

Embodiment B is a composition for treating cancerous cells in a subject having an immune system, comprising: a virus in the *Yatapoxvirus* genus having at least one mutation, wherein the at least one mutation results in suppressed expression of thymidine kinase (TK).

The composition of Embodiment B wherein the virus is a poxvirus which encodes a transgene expressing a bacterial flaggelin protein.

The composition of Embodiment B or Embodiment B with one or more of the intervening features wherein the transgene is a product of the *Salmonella enteric serovar typhimurium* gene ("fliC").

The composition of Embodiment B or Embodiment B with one or more of the intervening features wherein the virus is a tanapoxvirus (TPV), and wherein the at least one mutation suppresses expression of the thymidine kinase encoded by a 66R gene of the TPV.

The composition of Embodiment B or Embodiment B with one or more of the intervening features wherein the virus has a second mutation, and wherein a second mutation results in suppressed expression of a TNF binding protein by the virus.

The composition of Embodiment B or Embodiment B with one or more of the intervening features wherein the virus is a tanapoxvirus (TPV), and wherein a second mutation suppresses expression of the TNF binding protein encoded by a 2L gene of the TPV.

The composition of Embodiment B or Embodiment B with one or more of the intervening features wherein the virus to suppress expression of the TNF binding protein has a structure capable of binding to an MHC-1 light chain.

The composition of Embodiment B or Embodiment B with one or more of the intervening features wherein the virus further encodes a transgene to increase apoptosis of the cancerous cells.

The composition of Embodiment B or Embodiment B with one or more of the intervening features wherein the virus further encodes a transgene to activate the immune system of the subject.

Embodiment C is a method of delivering at least one gene to cancerous cells in a subject, comprising: modifying a virus of the *Yatapoxvirus* genus by mutating the virus to suppress expression of a TNF binding protein having a structure capable of binding an MHC-1 light chain; and administering the modified *Yatapoxvirus* genus virus to the subject systemically.

The method of Embodiment C further comprising: modifying the virus by encoding the at least one gene in the virus, wherein the at least one gene results in increased apoptosis of the cancerous cells or activates an immune response in the subject.

DETAILED DESCRIPTION OF EXPERIMENTS

OMK (Owl Monkey kidney) cells, HCT 116, SK-MEL-3, MDA-MB-231, COLO 205, SW1463 and WiDr cell lines from the American Type Culture Collection were used (available as American Type Culture Collection product numbers CRL-1556, CCL-247, CCL-222, CCL-234 and CCL-218 respectively). OMK cells were used for the virus amplification and viral titrations described herein. The cell lines were propagated in complete growth medium consisting of DMEM (available from Gibco/Life Technologies) supplemented with 10% (vol/vol) fetal bovine serum (available from Atlanta Biologicals), 2 mM L-glutamine (available from Sigma-Aldrich) and 50 μg/ml gentamicin sulfate (available from AMRESCO). After virus infection, cell monolayers of the cell lines were maintained in maintenance medium, which was identical to growth medium except that the concentration of fetal bovine serum was reduced to 2%. The cells were incubated at 37° C. in a 5% $CO_2$ atmosphere. Cell counting and cell viability assays were done with an Improved Neubauer hemacytometer using 0.2% (wt/vol) trypan blue. The SK-MEL-3 melanoma cells were cultured in growth medium consisting of McCoy's 5A medium (Sigma-Aldrich) with 15% FBS. McCoy's 5A medium with no serum was used as starving medium for melanoma growth.

Experiment 1: Control

Wild-type TPV (Kenya strain) was provided by Dr. Joseph Esposito (of the Centers for Disease Control, Atlanta, Ga., USA). The wild-type TPV was modified as described herein to form a control recombinant TPV which expresses the fluorescent reporter EGFP (with no other genetic modifications). Briefly, two identical vaccinia virus (VACV)-derived early/late synthetic promoters were used to drive the expression of a fluorescent reporter gene in the control recombinant TPV using the p2KO method. A p2KO expression cassette (including left and right flanks, plus the intervening open reading flames (ORF) and the promoters) was transferred to the viral genome of the wild-type TPV through a homologous recombination double-crossover event during a transfection/infection procedure, to form the control recombinant TPV. Flanking regions for recombination were ligated into the p2KO vector between the Sac I restriction site and the Not I restriction site on the 5'-(left) flank, and between the EcoR I restriction site and the Hind III restriction site on the 3'-(right) flank

Experiment 2: Transfection/Infection Procedure

A transfection/infection procedure was used to produce the recombinant TPV used in these example embodiments. Briefly, OMK cells were transfected using a jetPRIME transfection reagent (available from PolyPlus Transfection SA) at a concentration of 1 μl transfection reagent per μg of purified p2KO vector according to the manufacturer of the transfection reagent's transfection protocol. At approximately 5 hours post transfection, OMK monolayers were inoculated with 1 plaque-forming unit per cell (pfu/cell) of wild-type TPV-Kenya strain (non-fluorescent). At five days post-inoculation the infected monolayers were scraped with a rubber cell scraper on ice, subjected to three cycles of freezing and thawing at −80° C., 15 seconds of sonication at 4° C., serially diluted and plated onto freshly-seeded OMK monolayers at approximately 90% confluence and overlaid with maintenance medium containing 0.5% methylcellulose. Fluorescent, well-separated plaques were picked and each pick subjected to at least three rounds of plaque purification to produce a virus preparation which contained no visible wild type (non-fluorescent) plaques. Samples were considered pure only if no wild-type plaques were visible in culture and no wild-type TPV DNA was detectable by PCR.

Experiment 3: Confirmation of Viral Transgene Expression

Verification of FliC expression was done by Western blot. Verification of mCCL2 and mGM-CSF expression was done by Luminex multianalyte cytokine detection assay (performed by the University of Maryland cytokine core laboratory). Samples for analysis were prepared by infecting semi-confluent OMK cell monolayers in 60 mm tissue culture dishes (having 22.1 cm² surface area available for cell growth) with TPV-p2KO/Δ66R/mCCL2, TPV-p2KO/Δ66R/mGM-CSF, and TPV-p2KO/Δ2L/Δ66R/fliC using 10 pfu/cell. Supernatant (3 ml/dish) and cytoplasmic extracts were prepared at the indicated times post-infection. For FliC detection, extracted lysates were analyzed by Western blot. Proteins were transferred to a PVDF membrane (available from Millipore) and probed with an anti-FliC monoclonal antibody (available from BioLegend) at a 1:2000 dilution (vol/vol). Powdered milk 5% (wt/vol) was used as the blocking agent. The secondary antibody was a monoclonal anti-mouse IgG conjugated to horseradish peroxidase (available from Abcam), used at a 1:2500 dilution. Visualization was by ECL (Thermo Scientific/Pierce). Embodiments of TPV recombinants containing the p2KO vector but without a fliC, mGM-CSF or mCCL2 insert served as controls.

Experiment 4: Cell Density Determinations

Four human colorectal cancer cell lines, and the OMK cell control were separately inoculated into 12-well plates (3 wells per cell line) such that one day later the cells would achieve 90% confluency. Each well (having 3.8 cm² surface area available for cell growth) was trypsinized, counted and scored for viability by trypan blue exclusion. This was done to ensure that experiments at a specified number of viral pfu/cell for each cell line would be accurate.

For the human melanoma cancer lines, the cells were incubated at 37° C. in a 5% $CO_2$ atmosphere. All cell counting and viability assays were conducted using an Improved Neubauer hemacytometer and 0.2% (w/v) trypan blue in a normal saline solution.

For the human breast cancer lines, the cells were incubated at 37° C. in a 5% $CO_2$ atmosphere. All cell counting and viability assays were conducted using the Cell Counting Kit-8 for measuring cell proliferation. This kit is a replacement for $^3$H-Thymidine incorporation (CCK-8, Dojindo Molecular Technologies, Inc., 30 West Gude Dr., Suite 260, Rockville, Md. 20850).

Experiment 5: Virus Titration

To assay the number of viable recombinant TPV virions present in a sample, a plaque assay was used. Briefly, virus samples were sonicated for 15 seconds on ice, serially diluted in maintenance medium and inoculated onto nearly confluent OMK monolayers in 6-well plates (n=3 for each dilution of sample). Virus was allowed to adsorb at room temperature with gentle rocking for one hour. The inoculum was then removed and each well gently washed two times with 1 ml of pre-warmed maintenance medium. After washing, 2 ml of an overlay medium was added and the infected OMK monolayers incubated for 10 days at 37° C. The overlay medium was then removed and monolayers were stained (using 0.1% crystal violet in 37% formaldehyde). Plates were washed with distilled water, dried in air, and plaques were counted.

Experiment 6: Animals

For the colorectal cancer lines, male neonatal athymic nude (Nude-Foxn1$^{nu/nu}$) mice (available through Harlan Laboratories) were received at four weeks of age and allowed to acclimate for one week before the beginning of experimentation. Mice were individually housed in clear polycarbonate cages under a 12 hour/12 hour light/dark cycle. Food and water was available ad libitum. All animal housing conditions, manipulations and treatments were performed in accordance with the protocols approved by the Institutional Animal Care and Use Committee of Western Michigan University (IACUC protocol number 13-07-01).

For the breast and melanoma cancer lines, male athymic nude mice (Crl:NU(NCr)-Foxn1$^{nu}$) were purchased from Charles River company (Wilmington, Mass., USA) at 6-8 weeks of age. Mice were housed individually with food and water available in pathogen-free animal facility. All animal housing conditions, manipulations and treatments were performed in accordance with the protocols approved by the Institutional Animal Care and Use Committee of Western Michigan University (IACUC protocol number 13-07-01).

Experiment 7: Choice of Cell Line for Tumor Xenografts in Nude Mice

Before initiating in vivo studies in athymic nude mice, we determined which hCRC cell line had the highest viral productivity when infected with TPV/egfp. TPV/egfp was assayed for its ability to replicate in four hCRC-derived cell lines: HCT 116, SK-MEL-3, MDA-MB-231, WiDr, SW1463 and COLO 205. OMK cells were used as a positive control. Each cell line was seeded into 12-well tissue culture plates (having 3.8 cm$^2$ surface area available for cell growth) and 0.1 pfu/cell of TPV/egfp was inoculated into each well. Lysates were collected at 4 days post-infection and assayed by plaque assay.

Experiment 8: Tumor Induction and Measurement

Tumors were produced in athymic nude mice by subcutaneous injection of 5×10$^6$ HCT 116 cells on the dorsal surface, approximately above the first lumbar vertebra. Each injection was followed by an assessment of viability by trypan blue exclusion to ensure that the cells were viable at and after the time of injection. Once visible, tumors were measured using a digital caliper (Pittsburgh model 6ZBT-MCO) along a major axis (length), a minor axis (width) and a z dimension (height). The volume of the tumors was then estimated using formula 1 presented herein. When the estimation of tumor size reached or surpassed 75 mm$^3$ each animal was randomly segregated into the control group (group a) or one of the seven experimental groups (groups b-h).

Experiment 9: Virotherapy of HCT 116 Xenografts in Nude Mice

Each treatment group was composed of five or six tumor-bearing athymic nude mice. A single virotherapeutic injection was administered to each tumor-bearing mouse once tumor volume reached or exceeded 75 mm$^3$. Virotherapeutic injections were given intratumorally as a single injection of 5×10$^6$ pfu suspended in 100 μl of crude OMK cell lysate diluted in normal saline. Each mouse's weight and tumor volume was measured and recorded at three-day intervals thereafter. Data was collected for 13 time points over a total of 39 days. To control for unanticipated inflammation or other injection effects produced by the administration of the recombinant TPV injection, a vehicle control group was used, denoted as group a herein. This control group consisted animals which received the HCT 116 cells but experienced only a mock recombinant TPV injection (100 I 1 of vehicle only). This group is referred to as the "mock virotherapy" group or group A. All experimental groups were compared to group A to assess the therapeutic efficacy of the recombinant TPV.

To assess treatment effects each experimental group was compared to the control group a using the Mann-Whitney U test (sometimes referred to as the Wilcoxon rank-sum test). Treatment with the recombinant TPV was judged to have produced a significant therapeutic effect if the average tumor volume within a group was significantly reduced when compared to the mock-injected control. A significance level of $p<0.05$ was used throughout the study.

Result: The p2KO Poxvirus Ablation/Insertion Vector

Figure 3:
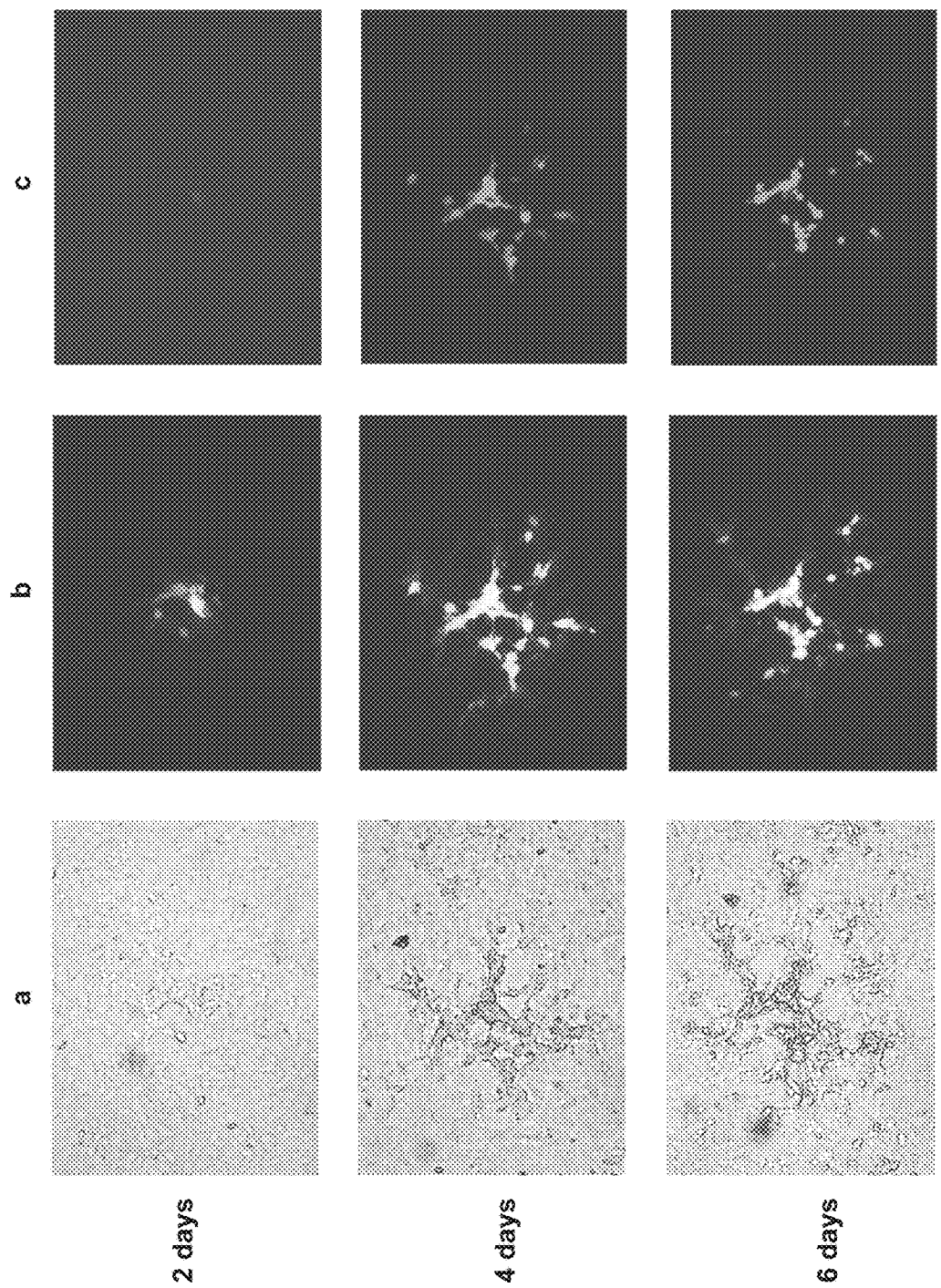
FIG. 3 includes views of one embodiment of a viral plaque at 2 days, 4 days, and 6 days produced by infection of one embodiment of a recombinant TPV which has been altered to express fluorescent reporters.

The p2KO poxvirus ablation/insertion vector was designed and constructed to provide a rapid and reliable way to simultaneously ablate any desired TPV gene(s) and replace the ablated gene(s) with the desired expressed fluorescent reporter and/or the desired expressed transgene. Visualization of viral infection in cultured cells was greatly facilitated by the inclusion of the fluorescent reporters, mCherry and EGFP. The use of two fluorescent reporters made it possible to identify and isolate the double-deleted recombinant TPV with the fliC insertion (TPV-p2KO/Δ2L/66R/fliC). A viral plaque produced by infection with the TPV-p2KO/Δ2L/Δ66R/fliC virus on an OMK cell monolayer is shown in FIG. 3, and demonstrates the simultaneous expression of the brilliant orange-red and green color associated with mCherry and EGFP, respectively.

The overall sequence of a base vector (i.e., with the fluorescent reporter but without the optional transgene to be expressed) was verified by DNA sequencing of an amplicon produced by PCR amplification of the region between the M13 forward and reverse primer binding sequences. The insertion of ORFs encoding mCCL2, mGM-CSF, or fliC was verified by DNA sequencing of the p2KO vector to ensure correct placement and orientation before they were used in the transfection/infection procedure. The recombinant TPVs were verified to be knockouts for either 2L, 66R, or both by agarose gel analysis of PCR products using recombinant viral DNA as a template.

Results: Transfection/Infection

By 4-5 days post-inoculation, expression of the fluorescent reporter was evident in the OMK cell monolayer, indicating gene expression from the p2KO vector in the cytosolic compartment of wild-type TPV-infected cells. In control cultures which were transfected with the p2KO vector but not subsequently inoculated with wild type TPV, no fluorescence was observed. Purity of the viral sample was then verified by PCR using the recombinant viral genomic DNA as the template before further use. All viral DNA samples were probed for the presence of the ampicillin resistance gene, which was not detected in any recombinant TPV. This indicates that all of the recombinant TPVs resulted from a double-crossover event rather than a single-crossover event.

Results: Confirmation of Viral Transgene Expression

To demonstrate that the inserted ORFs were expressed in cells infected with the recombinant TPVs (including TPV-p2KO/Δ66R/mCCL2, p2KO/Δ66R/mGM-CSF, and TPV-p2KO/Δ2L/Δ66R/fliC) OMK monolayers in 60 mm dishes (having 20 $cm^2$ growth area) were inoculated with the relevant recombinant TPV and assayed for transgene expression in cell lysates and culture supernatants as described previously. A Western blot of lysates from OMK cells inoculated TPV-p2KO/Δ2L/Δ66R/fliC was probed with a monoclonal anti-FliC antibody. A single band with an apparent molecular mass of 50 kDa was observed, identical to the FliC positive control, as expected. The intensity of this band gradually increased between day three and day six post-infection. The FliC transgene was not detected in mock infected cells. Infected cell lysates and their culture supernatants were assayed to determine the presence of mCCL2 and mGM-CSF. Both transgenes were highly expressed, and present in large amounts in infected cell supernatants (4.9 ng/ml mCCL2, and greater than 10.0 ng/ml mGM-CSF). Both mGM-CSF and mCCL2 were only weakly detectable or undetectable in cytoplasmic extracts of infected cells or control uninfected cells, and in cells infected with TPVs not expressing these transgenes. This data indicates that both mCCL2 and mGM-CSF were secreted from infected cells, as anticipated, while FliC accumulated within the cytoplasm of infected cells, again as anticipated.

Results: Cell Density Determinations

Each cell line used in this study had its confluent density (cells/$cm^2$) determined at near confluence. The OMK control cell line had a confluent density of approximately $1.0\times10^5$ cells/$cm^2$. The densities determined for the colorectal cancer cell lines were as follows: HCT 116 had a confluent density of approximately $1.4\times10^5$ cells/$cm^2$; COLO205 had a confluent density of approximately $6.9\times10^5$ cells/$cm^2$; SW1463 had a confluent density of approximately $4.5\times10^5$ cells/$cm^2$; WiDr had a confluent density of approximately $2.5\times10^5$ cells/$cm^2$. These values were used to calculate the number of pfu to use when inoculating these cell lines.

Results: Virotherapy HCT 116 Xenografts in Nude Mice

Before initiating in vivo studies in athymic nude mice, OMK cells were found to be the hCRC cell line with the highest viral productivity when infected with TPV/egfp, as described above. OMK cells were the best host cells, allowing the production of approximately $3\times10^6$ progeny pfu/well. Of the hCRC cell lines tested, HCT 116 produced the most progeny virions with an average yield (n=3) of approximately $7\times10^5$ progeny pfu/well. We therefore chose HCT 116 for the in vivo phase of this study.

In order to evaluate the oncolytic potential of the recombinant TPV, tumors were induced in athymic nude mice (Nude-Foxn1$^{nu/nu}$). Viability counts of the HCT 116 cells demonstrated that >99% were viable at the time of injection. Tumors generally reached 75 $mm^3$ within one to three weeks after injection of the HCT 116. Treatment with TPV/66R (group F), TPV/Δ2L (group G), and TPV/Δ2L/Δ66R/fliC (group H) all produced significant reductions in tumor size at 2 or more time points when compared to the mock injected controls. TPV/Δ2L-treated tumors (group G) were significantly smaller than mock-injected tumors at two time points, 33 days (a 47.6% reduction) and 36 days (a 65.2% reduction) post-treatment. TPV/Δ66R-treated tumors (group F) were significantly smaller than mock-injected tumors at two time points, 27 days (a 34.9% reduction) and 36 days (a 52% reduction) post-treatment. TPV/Δ2L/Δ66R/fliC-treated tumors (group H) showed a robust and durable therapeutic effect, and were significantly reduced in volume when compared to mock-injected tumors at six time points, 15 days (a 56.1% reduction), 21 days (a 62.0% reduction), 24 days (a 63.8% reduction), 27 days (a 59.5% reduction), 33 days (a 55.3% reduction) and 36 days (a 69.6% reduction) post-treatment.

Result: Virotherapy SK-MEL-3 Xenografts in Nude Mice

Melanoma tumors were induced in athymic nude mice via injecting $5\times10^6$ SK-MEL-3 cells subcutaneously on the dorsal surface in the inter-scapular region. When the tumor sizes developed to 45±4.5 $mm^3$, the mice were randomized into 4 groups and treated respectively with intratumoral injection of mock (only medium), wtTPV, TPVΔ66R, TPVΔ15L, TPVΔ15LΔ66R, and TPVΔ66R/mIL-2. As shown in FIGS. 4A-4E, the average tumor sizes in the animals treated with TPVΔ66R/mIL-2 were significantly smaller than those in the mice treated with mock injection. Furthermore, the volumes of tumors in TPVΔ66R/mIL-2-treated mice were smaller than those in wtTPV- or TPVΔ66R-treated mice, and the difference was statistically significant (P<0.05). The mean tumor volume of the tumors treated with TPVΔ66R/mIL-2 increased from around 45 $mm^3$ in day 0 (the day of treatment) to 64 $mm^3$ in day 35, while the mean tumor volume of tumors treated with mock medium injection increased from 46 $mm^3$ in day 0 to 310 $mm^3$ in day 35. The mean tumor volume of the tumors treated with wtTPV increased from 45 $mm^3$ in day 0 to 153 $mm^3$ in day 35, while the mean tumor volume of tumors treated with TPVΔ66R increased from 45 $mm^3$ in day 0 to 155 $mm^3$ in day 35. In light of the attenuated replication kinetics of TPVΔ66R/mIL-2 compared to wtTPV and TPVΔ66R indicated by in vitro studies, the in vivo results highly suggest the immuno-stimulatory effect of IL-2 in eliciting innate immune response for tumor reduction, in addition to the direct viral cytolysis.

Results: Virotherapy MDA-MB-231 Xenographs in Nude Mice

Breast cancer tumors were induced in athymic nude mice via injecting $5\times10^6$ MDA-MB-231 cells subcutaneously on the dorsal surface in the inter-scapular region. When the tumor sizes developed to 45±4.5 $mm^3$, the mice were randomized into 4 groups and treated respectively with intratumoral injection of mock (only medium), wt-TPV, TPV/Δ66R/mCCL2(mMCP1), TPV/Δ66R, TPV/Δ66R/mIL-2, TPV/Δ66R/mGMCSF, TPV/Δ2L, TPV/Δ66R/FliC, TPV/Δ66R/Δ2L, TPV/Δ66R/Δ2L/FliC, TPV/Δ15L. As shown in FIGS. 5A-5J, the average tumor sizes in the animals treated with recombinant TPV were significantly smaller than those in the mice treated with mock injection. Furthermore, the volumes of tumors in recombinant TPV treated mice were smaller than those in the wtTPV and mock injection treated mice, and the difference was statistically significant (P<0.05). The mean tumor volume of the tumors treated for each of the recombinant TPV variants are shown in FIGS. 5A-5J. The TPV recombinants were capable of infecting and replicating in human breast cancer cells, although ablation of the TK gene reduced the replication ability of the virus. The TPV recombinants significantly reduced the cell viability of human breast cancer cells in a dose dependent manner and significant regression was observed for the hTNBC (2L), TPV/Δ66R/mCCL2

(mMCP1), and TPV/Δ66R/mIL-2 recombinants. In light of the attenuated replication kinetics of the recombinant TPVs indicated by in vitro studies, the in vivo results highly suggest the immuno-stimulatory effect of these recombinant TPVs elicit innate immune response for tumor reduction, in addition to the direct viral cytolysis.

Although initial testing was performed using human colorectal cancer cell lines, the pharmaceutical virotherapy described herein is intended for use in treating a broad array of cancers. A non-limiting list of cancers to be treated with a pharmaceutical composition as described herein includes: basal cell carcinoma, carcinoma, choriocarcinoma, glioma tumor, intra-epithelial neoplasm, leukemia, lymphoma, Hodgkin's lymphoma, Non-Hodgkin's lymphoma, melanoma, myeloma, neuroblastoma, retinoblastoma, rhabdomyosarcoma, sarcoma, and cancers of the biliary tract, bladder, bone, brain, breast, CNS, cervix, colon and rectum, connective tissue, digestive system, endometrial cells, esophagus, eye, stomach, head and neck, kidney, larynx, liver, lung, pancreas, prostate, oral cavity, ovaries, respiratory system, skin, stomach, testicles, thyroid, uterus, and urinary system.

The pharmaceutical composition as described herein is to be administered at a therapeutically effective dose. The term "therapeutically effective dose" as used herein refers to an amount of the pharmaceutical which, after administration, is effective to achieve the desired therapeutic result. A therapeutically effective dose can vary from patient to patient according to factors such as the disease state, age, sex, and weight of the individual, form of the pharmaceutical, and the ability of the dosage form to elicit the desired response in the individual. The therapeutically effective dose may be determined by starting with a low, safe dose and escalating to higher doses, while monitoring for therapeutic effects (e.g. a reduction in cancer cell growth) along with the presence of any deleterious side effects. The pharmaceutical composition may include the poxvirus, viral nucleic acids, or expression vectors to produce the desired virotherapuetic effect.

The pharmaceutical composition can be administered via any suitable dosage forms or routes known in the art, including without limitation, parenteral, oral, enteral, buccal, nasal, topical, rectal, vaginal, transmucosal, epidermal, transdermal, dermal, ophthalmic, pulmonary, and subcutaneous administration routes to provide a systemic or localized, therapeutically effective dose. The pharmaceutical will be administered to a subject in formulations or preparations suitable for the particular administration route. Formulations suitable for administration of the pharmaceutical dosage form may include, without limitation; aerosols, dispersions, emulsions, implants, liposome based formulations, nose drops, patches, powders, solutions, sprays, suppositories and suspensions. The formulations may be presented in unit dosage form and may be prepared by any methods known in the art. Methods of preparing these formulations or dosage forms include the step of combining the poxvirus or nucleic acid of the present disclosure with one or more pharmaceutically acceptable carriers and may further comprise additives, such as without limitation: stabilizers, preservatives, and transfection facilitating agents which assist in the cellular uptake of the medicines. Suitable stabilizers may include, without limitation: albumin, EDTA, glycine and monosodium glutamate. Suitable preservatives may include, without limitation: antibiotics, methyl hydroxybenzoate, phenols, 2-phenoxyethanol, potassium sorbate, sodium benzoate, and thimerosal.

The pharmaceutical composition can be delivered locally into the target tissue or organ at a tumor site of a subject in need of treatment. An effective dose of the composition is directly injected to the tumor site through the subject's skin or in an exposed surgical field using a syringe. In certain embodiments, the pharmaceutical composition can be injected using an implantable dosing device.

It is also important to note that the construction and arrangement of the elements of the composition as shown and described in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

What is claimed is:

1. A composition, comprising:
a virus in the *Yatapoxvirus* genus for treating cancerous cells in a subject having an immune system having at least one mutation, wherein the at least one mutation results in a loss of expression of a TNF binding protein by the virus.

2. The composition of claim 1, wherein the virus results in a loss of expression of the TNF binding protein that has a structure capable of binding to an MHC-1 light chain.

3. The composition of claim 1, wherein the virus is a *Yatapoxvirus* which encodes a transgene expressing a bacterial flaggelin.

4. The composition of claim 3, wherein the transgene is a product of the *Salmonella enterica* serovar *typhimurium* gene ("fliC").

5. The composition of claim 1, wherein the virus is a tanapoxvirus (TPV), and wherein the at least one mutation results in a loss of expression of the TNF binding protein encoded by a 2L gene of the TPV.

6. The composition of claim 1, wherein the virus has a second mutation, and wherein the second mutation results in a loss of expression of thymidine kinase by the virus.

7. The composition of claim 1, wherein the virus is a tanapoxvirus (TPV), and wherein a second mutation results in a loss of expression of thymidine kinase encoded by a 66R gene of the TPV.

8. The composition of claim 1, wherein the virus further encodes a transgene to activate the immune system of the subject.

9. The composition of claim 1, wherein the virus further encodes a transgene to increase apoptosis of the cancerous cells.

10. A composition, comprising:
a virus in the *Yatapoxvirus* genus for treating cancerous cells in a subject having an immune system having at least two mutations, wherein a first mutation results in a loss of expression of thymidine kinase (TK) and a second mutation results in a loss of expression of a 15-L encoded protein that mimics neuregulin.

11. The composition of claim 10, wherein the virus is a *Yatapoxvirus* which encodes a transgene expressing a bacterial flaggelin protein.

12. The composition of claim 11, wherein the transgene is a product of the *Salmonella enterica* serovar *typhimurium* gene ("fliC").

13. The composition of claim 10, wherein the virus is a tanapoxvirus (TPV), and wherein the first mutation results in a loss of expression of the thymidine kinase encoded by a 66R gene of the TPV.

14. The composition of claim 10, wherein the virus has a third mutation, and wherein the third mutation results in a loss of expression of a TNF binding protein by the virus.

15. The composition of claim 10 wherein the virus is a tanapoxvirus (TPV), and wherein a third mutation results in a loss of expression of the TNF binding protein encoded by a 2L gene of the TPV.

16. The composition of claim 15, wherein the virus to results in a loss of expression of the TNF binding protein that has a structure capable of binding to an MHC-1 light chain.

17. The composition of claim 10, wherein the virus further encodes a transgene to increase apoptosis of the cancerous cells.

18. The composition of claim 10, wherein the virus further encodes a transgene to activate the immune system of the subject.

19. A method of delivering at least one gene to cancerous cells in a subject, comprising:
modifying a virus of the *Yatapoxvirus* genus by mutating the virus to result in a loss of expression of a TNF binding protein having a structure capable of binding an MHC-1 light chain; and
administering the modified *Yatapoxvirus* genus virus to the subject systemically.

20. The method of claim 19 further comprising:
modifying the virus by encoding at least one gene in the virus, wherein the at least one gene results in increased apoptosis of the cancerous cells or activates an immune response in the subject.

* * * * *

UNITED STATES PATENT AND TRADEMARK OFFICE
CERTIFICATE OF CORRECTION

PATENT NO. : 10,434,189 B2
APPLICATION NO. : 15/407912
DATED : October 8, 2019
INVENTOR(S) : Essani et al.

It is certified that error appears in the above-identified patent and that said Letters Patent is hereby corrected as shown below:

In the Specification

Column 10, Line 53:
"5'-AATGGATCACATAAAG<u>GAGCTCT</u>TAAACG-3'" should be
--5'-AATGGATCACATAAAG<u>GAGCTC</u>TTAAACG-3'--.

Column 11, Line 17:
"5'-TAGGCCTG<u>GGATCC</u>GATCCACCGGTCGCCACC<u>ATG</u>CAGGTCCCTC-3'" should be
--5'-TAGGCCTG<u>GGATCC</u>GATCCACCGGTCGCCACC<u>ATG</u>CAGGTCCCTG-3'--.

Column 12, Line 58:
"100 L" should be --100 μL--.

Column 16, Line 59:
"g/animal" should be --μg/animal--.

Column 22, Line 18:
"I 1" should be --μl--.

Column 22, Line 31:
"Result:" should be --Results:--.

Column 22, Lines 41-42:
"(TPV-p2KO/Δ2L/66R/fliC)" should be --(TPV-p2KO/Δ2L/Δ66R/fliC)--.

Column 23, Line 62:
"TPV/66R" should be --TPV/Δ66R--.

Column 24, Line 13:
"Result:" should be --Results:--.

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,434,189 B2

In the Claims

Column 36, Line 29 Claim 16:
Delete "to".

SEQUENCE LISTING

<160> NUMBER OF SEQ ID NOS: 10

<210> SEQ ID NO 1
<211> LENGTH: 1500
<212> TYPE: DNA
<213> ORGANISM: Bacterial Salmonella typhimurium
<220> FEATURE:
<221> NAME/KEY: Gene
<222> LOCATION: (1)..(1500)
<223> OTHER INFORMATION: Fli.C

<400> SEQUENCE: 1

```
aaggaaaaga tcatggcaca agtcattaat acaaacagcc tgtcgctgtt gacccagaat      60
aacctgaaca atcccagtc cgctctgggc accgctatcg agcgtctgtc ttccggtctg       120
cgtatcaaca gcgcgaaaga cgatgcggca ggtcaggcga ttgctaaccg ttttaccgcg      180
aacatcaaag gtctgactca ggcttcccgt aacgctaacg acggtatctc cattgcgcag      240
accactgaag gcgcgctgaa cgaaatcaac aacaacctgc agcgtgtgcg tgaactggcg      300
gttcagtctg ctaacagcac caactcccag tctgacctcg actccatcca ggctgaaatc      360
acccagcgcc tgaacgaaat cgaccgtgta tccggccaga ctcagttcaa cggcgtgaaa      420
gtcctggcgc aggacaacac cctgaccatc caggttggtg ccaacgacgg tgaaactatc      480
gatatcgatc tgaagcagat caactctcag accctgggtc tggatacgct gaatgtgcaa      540
caaaaatata aggtcagcga tacggctgca actgttacag atatgccga tactacgatt       600 gctttagaca atagtacttt taaagcctcg gctactggtc ttggtggtac tgaccagaaa      660
attgatggcg attttaaaatt tgatgatacg actggaaaat attacgccaa agttaccgtt     720
acggggggaa ctggtaaaga tggctattat gaagtttccg ttgataagac gaacggtgag     780
gtgactcttg ctggcggtgc gacttccccg cttacaggtg gactacctgc gacagcaact     840
gaggatgtga aaaatgtaca agttgcaaat gctgatttga cagaggctaa agccgcattg     900
acagcagcag gtgttaccgg cacagcatct gttgttaaga tgtcttatac tgataataac      960
ggtaaaacta ttgatggtgg tttagcagtt aaggtaggcg atgattacta ttctgcaact      1020
caaaataaag atggttccat aagtattaat actacgaaat acactgcaga tgacggtaca      1080
tccaaaactg cactaaacaa actgggtggc gcagacggca aaaccgaagt tgtttctatt      1140
ggtggtaaaa cttacgctgc aagtaaagcc gaaggtcaca ctttaaagc acagcctgat      1200 ctggcggaag cggctgctac aaccaccgaa aacccgctgc agaaaattga tgctgctttg     1260
gcacaggttg acacgttacg ttctgacctg ggtgcggtac agaaccgttt caactccgct     1320
attaccaacc tgggcaacac cgtaaacaac ctgacttctg cccgtagccg tatcgaagat     1380
tccgactacg cgaccgaagt ttccaacatg tctcgcgcgc agattctgca gcaggccggt      1440
acctccgttc tggcgcaggc gaaccaggtt ccgcaaaacg tcctctcttt actgcgttaa      1500
```

<210> SEQ ID NO 2
<211> LENGTH: 510
<212> TYPE: DNA
<213> ORGANISM: Athymic nude mouse
<220> FEATURE:
<221> NAME/KEY: Gene
<222> LOCATION: (1)..(510)
<223> OTHER INFORMATION: mIL-2

<400> SEQUENCE: 2

```
atgtacagca tgcagctcgc atcctgtgtc acattgacac ttgtgctcct tgtcaacagc       60
gcacccactt caagctccac ttcaagctct acagcggaag cacagcagca gcagcagcag      120
```

```
cagcagcagc agcagcagca cctggagcag ctgttgatgg acctacagga gctcctgagc    180
aggatggaga attacaggaa cctgaaactc cccaggatgc tcaccttcaa attttacttg    240
cccaagcagg ccacagaatt gaaagatctt cagtgcctag aagatgaact tggacctctg    300
cggcatgttc tggatttgac tcaaagcaaa agctttcaat tggaagatgc tgagaatttc    360
atcagcaata tcagagtaac tgttgtaaaa ctaaagggct ctgacaacac atttgagtgc    420
caattcgatg atgagtcagc aactgtggtg gactttctga ggagatggat agccttctgt    480
caaagcatca tctcaacaag ccctcaataa                                     510

<210> SEQ ID NO 3
<211> LENGTH: 426
<212> TYPE: DNA
<213> ORGANISM: Athymic nude mouse
<220> FEATURE:
<221> NAME/KEY: Gene
<222> LOCATION: (1)..(426)
<223> OTHER INFORMATION: mGM-CSF

<400> SEQUENCE: 3
atgtggctgc agaatttact tttcctgggc attgtggtct acagcctctc agcacccacc     60
cgctcaccca tcactgtcac ccggccttgg aagcatgtag aggccatcaa agaagccctg    120
aacctcctgg atgacatgcc tgtcacgttg aatgaagagg tagaagtcgt ctctaacgag    180
ttctccttca gaagctaac atgtgtgcag acccgcctga agatattcga gcagggtcta    240
cggggcaatt tcaccaaaact caagggcgcc ttgaacatga cagccagcta ctaccagaca    300 tactgcccc caactccgga aacggactgt gaaacacaag ttaccaccta tgcggatttc    360
atagacagcc ttaaaacctt tctgactgat atccccttg aatgcaaaaa accaggccaa    420
aaatga                                                              426

<210> SEQ ID NO 4
<211> LENGTH: 447
<212> TYPE: DNA
<213> ORGANISM: Athymic nude mouse
<220> FEATURE:
<221> NAME/KEY: Gene
<222> LOCATION: (1)..(447)
<223> OTHER INFORMATION: mCCL-2

<400> SEQUENCE: 4
atgcaggtcc ctgtcatgct tctgggcctg ctgttcacag ttgccggctg gagcatccac     60
gtgttggctc agccagatgc agttaacgcc ccactcacct gctgctactc attcaccagc    120
aagatgatcc caatgagtag gctggagagc tacaagagga tcaccagcag caggtgtccc    180
aaagaagctg tagtttttgt caccaagctc aagagagagg tctgtgctga ccccaagaag    240
gaatgggtcc agacatacat taaaaacctg gatcggaacc aaatgagatc agaacctaca    300 actttatta aaactgcatc tgccctaagg tcttcagcac ctttgaatgt gaagttgacc    360
cgtaaatctg aagctaatgc atccactacc ttttccacaa ccacctcaag cacttctgta    420
ggagtgacca gtgtgacagt gaactag                                       447

<210> SEQ ID NO 5
<211> LENGTH: 462
<212> TYPE: DNA
<213> ORGANISM: Homo sapiens
<220> FEATURE:
<221> NAME/KEY: Gene
<222> LOCATION: (1)..(462)
```

<223> OTHER INFORMATION: IL-2

<400> SEQUENCE: 5

```
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat tacaagaatc ccaaactcac caggatgctc     180
acatttaagt tttacatgcc caagaaggcc acagaactga acatcttca gtgtctagaa      240
gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                        462
```

<210> SEQ ID NO 6
<211> LENGTH: 435
<212> TYPE: DNA
<213> ORGANISM: Homo sapiens
<220> FEATURE:
<221> NAME/KEY: Gene
<222> LOCATION: (1)..(435)
<223> OTHER INFORMATION: GM-CSF

<400> SEQUENCE: 6

```
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga tgaaacagt agaagtcatc      180
tcagaaatgt ttgacctcca ggagccgacc tgcctacaga cccgcctgga gctgtacaag     240
cagggcctgc ggggcagcct caccaagctc aaggcccct tgaccatgat ggccagccac     300
tacaagcagc actgccctcc aaccccggaa acttcctgtg caacccagat atcacctttt     360
gaaagtttca agagaaacct gaaggacttt ctgcttgtca tccccttga ctgctgggag     420
ccagtccagg agtga                                                      435
```

<210> SEQ ID NO 7
<211> LENGTH: 300
<212> TYPE: DNA
<213> ORGANISM: Homo sapiens
<220> FEATURE:
<221> NAME/KEY: Gene
<222> LOCATION: (1)..(300)
<223> OTHER INFORMATION: CCL-2

<400> SEQUENCE: 7

```
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
aaagaagctg tgatcttcaa gaccattgtg gccaaggaga tctgtgctga ccccaagcag     240
aagtgggttc aggattccat ggaccacctg gacaagcaaa cccaaactcc gaagacttga     300
```

<210> SEQ ID NO 8
<211> LENGTH: 552
<212> TYPE: DNA
<213> ORGANISM: Tanapoxvirus
<220> FEATURE:
<221> NAME/KEY: Gene
<222> LOCATION: (1)..(552)
<223> OTHER INFORMATION: Thymidine kinase/66R

```
<400> SEQUENCE: 8
atgacatcta aaagtggaca tatacagatt atattaggcc caatgttttc tggtaaaagt      60
acagaattaa ttagaatatt aaaacggtat caaattgcta ggtatacttg ctttgtaata     120
aaatactcaa aagatactag gtacggaaaa ggattagtaa cacacgataa taattcaata     180
cccgcaattc ctgttaactc actaagtgaa attaattgtg ataaaattaa agctgatgta     240
ataggaatag acgaaggaca attttttcca gatattgtag aattttgcga acgtatggca     300
aacgatggaa aaattgtaat agttgctgct ttagacggta catttttaag agagccattt     360
ggaaatattt taaaattaat accatgtgct gagtacgttt caaagcttac agccgtttgc     420
atgaattgtt ttaatagcgc atcgttttct aaacgaattg gagatgaaca agaaatagaa     480
gttataggag gcaaagacaa gtatcaatct gtatgtagaa aatgttactt taaattaaaa     540
ataaataatt ga                                                         552

<210> SEQ ID NO 9
<211> LENGTH: 1017
<212> TYPE: DNA
<213> ORGANISM: Tanapoxvirus
<220> FEATURE:
<221> NAME/KEY: Gene
<222> LOCATION: (1)..(1017)
<223> OTHER INFORMATION: 2L

<400> SEQUENCE: 9
atggataagt tactattatt tagcacaatt gtagcagttt gtaactgcat aactttaaaa      60
tataattata ctgttacgtt aaaagatgat gggttatacg atggagtatt ttacgatcat     120
tacaacgatc agttagtgac gaaaatatca tataaccatg aaactagaca cggaaacgta     180
aattttaggg ctgattggtt taatatttct aggagtcccc acacgccagg taacgattat     240
aactttaact tttggtattc tttaatgaaa gaaactttag aagaaattaa taaaaacgat     300
agcacaaaaa ctacttcgct ttcattaatc actgggtgtt atgaaacagg attattattt     360
ggtagttatg ggtatgtaga acggccaac gggccgttgg ccagatacca tacaggagat     420
aaaaggttta cgaaaatgac acataaaggt tttcccaagg ttggaatgtt aactgtaaaa     480
acactctttt ggaaagatgt aaaagcttat ttaggcggtt ttgaatatat gggatgttca     540
ttagctattt tagattacca aaaaatggct aaaggtaaaa taccaaaaga tacaacacct     600
acagtgaaag taacgggtaa tgagttagaa gatggtaaca tgactcttga atgcactgta     660
aattcatttt accctcctga cgtaattact aagtggatag aaagcgaaca tttttaaaggt     720 gaatataaat atgttaacgg aagatactat ccagaatggg ggagaaaatc caattatgag     780
ccaggagagc caggttttcc atggaatatc aaaaagata aagatgcaaa tacatatagt     840
ttaacagatt tagtacgtac aacatcaaaa atgagtagtc aaccagtatg tgttgttttc     900
catgacactt tagaagcgca agtttatact tgttctgaag gatgcaatgg agagctatac     960
gatcacctat atagaaaaac agaagaaggg gaaggtgaag aggatgaaga agactga       1017

<210> SEQ ID NO 10
<211> LENGTH: 234
<212> TYPE: DNA
<213> ORGANISM: Tanapoxvirus
<220> FEATURE:
<221> NAME/KEY: Gene
<222> LOCATION: (1)..(234)
<223> OTHER INFORMATION: 15L
```

```
<400> SEQUENCE: 10
atgaaaaaca aatttatgtt ttttacttta tcatgtgcca ttttagcatt aaattgttta          60
ccgttgctac aaaatatgta cgtaatagag tgtgacacaa gtaacttttg tttaaatgga         120
gggacctgtt ttttaactaa acatgttcct tcgtattcta attttagttt aaaattttgt         180
ttgtgtaaaa ggcaatttaa cggaaaaagg tgtgaaaata aaatagtaaa ttaa              234
```